United States Patent
Farber et al.

(10) Patent No.: US 11,160,878 B1
(45) Date of Patent: Nov. 2, 2021

(54) SUPRAMOLECULAR SYSTEMS BASED ON DYNAMIC SELF-ORGANIZING NANOSTRUCTURES WITH ANTIVIRAL PROPERTIES

(71) Applicants: Boris Farber, Brooklyn, NY (US); Artur Viktorovich Martynov, Kharkov (UA)

(72) Inventors: Boris Farber, Brooklyn, NY (US); Artur Viktorovich Martynov, Kharkov (UA)

( * ) Notice: Subject to any disclaimer, the term of this patent is extended or adjusted under 35 U.S.C. 154(b) by 0 days.

(21) Appl. No.: 16/936,667

(22) Filed: Jul. 23, 2020

Related U.S. Application Data

(60) Provisional application No. 63/037,577, filed on Jun. 10, 2020.

(51) Int. Cl.
*A61K 31/714* (2006.01)
*A61K 47/69* (2017.01)
(Continued)

(52) U.S. Cl.
CPC ............ *A61K 47/6949* (2017.08); *A61K 8/64* (2013.01); *A61K 9/5123* (2013.01);
(Continued)

(58) Field of Classification Search
CPC .................. A61K 47/6949; A61K 31/714
See application file for complete search history.

(56) References Cited

FOREIGN PATENT DOCUMENTS

WO    WO-2011130716 A2 * 10/2011 ............. A61K 45/06

OTHER PUBLICATIONS

Kwangjin An, et al. Synthesis and biomedical applications of hollow nanostructures, National Creative Research Initiative Center for Oxide Nanocrystalline Materials and School of Chemical and Biological Engineering, Seoul National University, Seoul. May 18, 2009. pp. 151-744. Republic of Korea.

(Continued)

*Primary Examiner* — Benjamin J Packard
(74) *Attorney, Agent, or Firm* — Daniel M. Cohn; Howard M. Cohn

(57) ABSTRACT

Methods of producing supramolecular structures using molecular recognition and methods of controlling the size of the nanoparticles produced to form discrete particles. Pharmaceutical formulations of the supramolecular structures for viral infections treatments. Supramolecular nanoparticles may comprise combinatorial carboxylated cobalamins; combinatorial carboxylated dipyridamoles; and basic amino acid polypeptides. The supramolecular nanoparticles are dynamic self-organizing soluble nanostructures which have a plurality of binding components, organic cores, and terminating components. The binding components include combinatorial carboxylated cobalamins with binding regions. The organic cores include combinatorial carboxylated dipyridamole adapted to bind to the combinatorial carboxylated cobalamins such that the organic cores can provide a mechanical structure for the self-organizing soluble nanostructures and a first type of inclusion complexes. The supramolecular nanoparticles include terminating components with at least one terminating binding element capable of binding to a residual binding region of a binding components.

30 Claims, 13 Drawing Sheets

(51) Int. Cl.
| | |
|---|---|
| A61K 9/51 | (2006.01) |
| A61K 31/525 | (2006.01) |
| A61P 31/14 | (2006.01) |
| A61K 31/7084 | (2006.01) |
| A61K 31/7076 | (2006.01) |
| A61P 31/22 | (2006.01) |
| A61K 8/64 | (2006.01) |
| A61K 48/00 | (2006.01) |

(52) U.S. Cl.
CPC .......... *A61K 9/5146* (2013.01); *A61K 31/525* (2013.01); *A61K 31/7076* (2013.01); *A61K 31/7084* (2013.01); *A61K 31/714* (2013.01); *A61K 47/6929* (2017.08); *A61K 47/6935* (2017.08); *A61K 48/00* (2013.01); *A61P 31/14* (2018.01); *A61P 31/22* (2018.01)

(56) References Cited

OTHER PUBLICATIONS

Anderson. Selective Photothermolysis: Precise Microsurgery by Selective Absorption of Pulsed Radiation. Science, Apr. 29, 1983. pp. 524-527. vol. 220.

Au. et al. A Quantitative Study on the Photothermal Effect of Immuno Gold Nanocages Targeted to Breast Cancer Cells. ACSNANO. org. vol. 2, No. 8. Jun. 14, 2008 pp. 1645-1652.

Bazin. et al. Electrophoretic silica-coating process on a nanostructured copper electrode. Aug. 18, 2008. Chem. Commun., 2008, pp. 5004-5006.

Chen, et al. Immuno Gold Nanocages with Tailored Optical Properties for Targeted Photothermal Destruction of Cancer Cells. Nano Letters. Feb. 12, 2007. pp.1318-1322. vol. 7, No. 5.

Chen, et al. Construction, DNA wrapping and cleavage of a carbon nanotube-polypseudorotaxane conjugate. The Royal Society of Chemistry. Apr. 3, 2009. pp. 4106-4108.

Cheng, et al. Nanopatterning self-assembled nanoparticle superlattices by moulding microdroplets. Sep. 28, 2008. pp. 682-690. Department of Biological & Environmental Engineering, Cornell University, Ithaca, New York 14853, USA.

Cheon, et al. Synergistically Integrated Nanoparticles as Multimodal Probes for Nanobiotechnology. Accounts of Chemical Research. Feb. 12, 2008. pp. 1630-1640. vol. 41, No. 12. Department of Chemistry, Yonsei University, Seoul.

Davis, et al. Nanoparticle therapeutics:an emerging treatment modality for cancer. Nature Reviews. Sep. 2008. pp. 771-782. vol. 7.

Dickerson, et al. Gold nanorod assisted near-infrared plasmonic photothermal therapy (PPTT) of squamous cell carcinoma in mice. Science Direct. pp. 57-66. School of Biology, Ovarian Cancer Institute, Georgia Institute of Technology, Atlanta, GA 30332-0400, USA.

Elghanian, et al. Selective Colorimetric Detection of Polynucleotides Based on the Distance-Dependent Optical Properties of Gold Nanoparticles. Science . Aug. 22, 1997. pp 1078-1081. Science 277.

Gao, et al. In vivo cancer targeting and imaging with semiconductor quantum dots. Nature Technology. Jul. 18, 2004. pp. 969-976. vol. 22, No. 8.

Glover, et al. Towards Safe, Non-Viraltherapeutic Gene Expression in Humans. Nature Reviews. pp. 299-311. vol. 6. Apr. 2005.

Gobin, et al. Near-Infrared Resonant Nanoshells for Combined Optical Imaging and Photothermal Cancer Therapy. Noano Letters. Jun. 6, 2007. pp. 1929-1934. vol. 7, No. 7.

Goverov et al. Generating heat with metal nanoparticles. Nano Today. pp. 30-38. vol. 2, No. 1. Department of Physics and Astronomy, and Department of Chemistry and Biochemistry, Ohio University, Athens, OH 45701, USA.

Gratton, et al. The Pursuit of a Scalable Nanofabrication Platform for Use in Material and Life Science Applications. Accounts of Chemical Research. pp. 1685-1695. vol. 41, No. 12.

Green, et al. A Combinatorial Polymer Library Approach Yields Insight into Nonviral Gene Delivery. Accounts of Chemical Research. May 29, 2008. pp. 749-759. vol. 41, No. 6.

Heath et al. Nanotechnology and Cancer. Annual Review of Medicine. Oct. 15, 2007. pp. 251-265. vol. 41, No. 6. Division of Chemistry and Chemical Engineering, California Institute of Technology, Pasadena, California.

Hu et al. Efficient NIR Hyperthermia and Intense Nonlinear Optical Imaging Contrast on the Gold Nanorod-in-Shell Nanostructures. J. Am. Chem. Soc.. Jun. 8, 2012. pp. 14186-14187. vol. 22 Issue 5.

Huang et al. Plasmonic photothermal therapy (PPTT) using gold nanoparticles. Lasers Med Sci. Apr. 26, 2007. pp. 217-228. Springer-Verlag London.

Huang et al. Selective Photothermal Therapy for Mixed Cancer Cells Using Aptamer-Conjugated Nanorods. Langmuir. Apr. 26, 2007. pp. 11860-11865. vol. 24, No. 20, 2008.

Jain et al. Noble Metals on the Nanoscale: Optical and Photothermal Properties and Some Applications in Imaging, Sensing, Biology, and Medicine. Accounts of Chemical Research. Dec. 17, 2007. pp. 1578-1586. vol. 41, No. 12.

Jun et al. Chemical Design of Nanoparticle Probes for High-Performance Magnetic Resonance Imaging. Angew. Chem. Int. Ed. 2008. pp. 5122-5135.

Katz et al. Integrated Nanoparticle-Biomolecule Hybrid Systems: Synthesis, Properties, and Applications. Angew. Chem. Int. Ed. pp. 6042-6108.

Khlebtsov et al. Optical amplification of photothermal therapy with gold nanoparticles and nanoclusters. Nanotechnology. Jul. 19, 2006. pp. 5167-5179.

Kim et al. Designed Fabrication of Multifunctional Magnetic Gold Nanoshells and Their Application to Magnetic Resonance Imaging and Photothermal Therapy. Nanomedicine. pp. 7918-7922. vol. 118.

Kim et al. Strategies for silencing human disease using RNA interference. Nature Publishing Group. pp. 173-184. vol. 8, 2007.

Klajn et al. Dynamic hook-and-eye nanoparticle sponges. Nature Chemistry. Nov. 15, 2009. pp. 733-738. vol. 1, 2009.

Kumar et al. Supramolecular-directed synthesis of RNA-mediated CdS/ZnS nanotubes. Chem. Commun. Apr. 14, 2009. pp. 5433-5435.

Lal et al. Nanoshell-Enabled Photothermal Cancer Therapy: Impending Clinical Impact. Accounts of Chemical Research. Jun. 26, 2008. pp. 1842-1851. vol. 41, No. 12.

Lapotko et al. Selective Laser Nano-Thermolysis of Human Leukemia Cells With Microbubbles Generated Around Clusters of Gold Nanoparticles. Lasers in Surgery and Medicine. Apr. 11, 2006. pp. 1631-1642.

Liang et al. Polymorphism of DNA-anionic liposome complexes reveals hierarchy of ion-mediated interactions. PNAS. Aug. 9, 2005. pp. 11173-11178. vol. 102, No. 32.

Lin et al. One-Dimensional Plasmon Coupling by Facile Self-Assembly of Gold Nanoparticles into Branched Chain Networks. Advanced Materials. Apr. 22, 2005. pp. 2553-2559.

Loo et al. Nanoshell-Enabled Photonics-Based Imaging and Therapy of Cancer. Technology in Cancer Research & Treatment. Dec. 22, 2003. pp. 33-40. vol. 3, No. 1.

Lu et al. Self-assembly and tunable plasmonic property of gold nanoparticles on mercapto-silica microspheres. Journal of Materials Chemistry. May 21, 2009. pp. 4597-4602.

Maye et al. Mediator-Template Assembly of Nanoparticles. J. Am. Chem. Soc. Sep. 14, 2004. pp. 1519-1529.

Mitragotri et al. NPhysical approaches to biomaterial design. Nature Materials. Dec. 19, 2008. pp. 15-23. vol. 8, Jan. 2009.

Napier et al. Nanoparticle Drug Delivery Platform. Polymer Reviews. Jan. 22, 2007. pp. 321-327. vol. 3, No. 1.

Nel et al. understanding biophysicochemical interactions at the nano-bio interface. Nature Materials. Jun. 14, 2009. pp. 543-557. vol. 8, Jul. 2009.

Nie et al. Nanotechnology Applications in Cancer. Annu. Rev. Biomed.. Apr. 17, 2007. pp. 258-280.

Niemeyer. Nanoparticles, Proteins, and Nucleic Acids: Biotechnology Meets Materials Science. Angew. Chem. Int. Ed. pp. 4128-4158.

(56) References Cited

OTHER PUBLICATIONS

Niidome et al. Gene Therapy Progress and Prospects: Nonviral vectors. Gene Therapy. pp. 1647-1652. vol. 3, No. 1.
Ofir et al. Polymer and biopolymer mediated self-assembly of gold nanoparticles. Chemical Society Reviews. Apr. 16, 2008. pp. 1814-1825. vol. 37, No. 9.
Pack et al. Design and Development of Polymers for Gene Delivery. Nature Reviews, pp. 581-593. vol. 4, Jul. 2005.
Prata et al. A new helper phospholipid for gene delivery. Chem. Commun., 2008. Oct. 22, 2007. pp. 1566-1568.
Richardson et al. Experimental and Theoretical Studies of Heating Effects in Metal Nanoparticle Solutions. Nano Letters. Dec. 6, 2008. pp. 1139-1146. vol. 9, No. 3.
Rosi et al. Nanostructures in Biodiagnostics. American Chemical Society. Nov. 23, 2004. pp. 1547-1562. 2005.
Choi et al. Renal clearance of quantum dots. Nature Biotechnology. Apr. 13, 2007. pp. 1165-1170. vol. 25, No. 10.
Torchilin, et al. Cell transfection in vitro and in vivo with nontoxic TAT peptide-liposome-DNA complexes. PNAS. Jan. 2003. pp. 1972-1977. vol. 100, No. 4.
Torchilin. Recent Advances Withliposomes as Pharmaceutical Carriers. Nature Reviews. Feb. 2005. pp. 145-160. vol 4.
Troutman, et al. Biodegradable Plasmon Resonant Nanoshells. Advanced Materials. pp. 2604-2608.
Woodrow et al. Intravaginal gene silencing using biodegradable polymer nanoparticles densely loaded with small-interfering RNA. Advanced Materials. pp. 526-533. vol. 8, Jun. 2009.
Zhuang, et al. Controlling Colloidal Superparticle Growth Through Solvophobic Interactions, pp.s-1-s10. Department of Chemistry, University of Florida, Gainesville, Florida 32611, USA.

* cited by examiner (F1)    $m\,A1 + k\,M2 + k\,M3 = m\,B$ (F2)    $k = n*(2^n - 1) = 4*(2^4 - 1) = 60$ (F3)    $m = 4*(3*2^{n-2} - 1) = 44$

SUPRAMOLECULAR SYSTEMS BASED ON DYNAMIC SELF-ORGANIZING NANOSTRUCTURES WITH ANTIVIRAL PROPERTIES

BACKGROUND OF THE INVENTION

Field of Invention

The invention relates to supramolecular nanoparticles prepared using molecular recognition properties of combinatorial chemical building blocks to self-assembly into the nanoparticles, and methods of controlling the size of the nanoparticles produced. The invention also includes methods of using the supramolecular structures for viral infections treatment.

Discussion of Related Art

There is a predictability only for simple models of molecular structure. Chemists have mistakenly become complacent with paradigms of molecular structure to such an extent that validity and the limit of usefulness of many kinds of chemistry is taught to be predictable.

Chemists are now seeking models for molecular structure usefulness beyond individual molecules and looking to chemical synthesis and composition utilities at the supramolecular level. Supramolecular chemistry (Wikipedia, 2020) is a domain of chemistry concerning chemical systems composed of a discrete number of molecules. The strength of the forces responsible for spatial organization of the system range from weak intermolecular forces, electrostatic charge, or hydrogen bonding to strong covalent bonding, provided that the electronic coupling strength remains small relative to the energy parameters of the component. [Whereas traditional chemistry concentrates on the covalent bond, supramolecular chemistry examines the weaker and reversible non-covalent interactions between molecules. These forces include hydrogen bonding, metal coordination, hydrophobic forces, van der Waals forces, pi-pi interactions and electrostatic effects.

Important concepts advanced by supramolecular chemistry include molecular self-assembly, molecular folding, molecular recognition, hostguest chemistry, mechanically-interlocked molecular architectures, and dynamic covalent chemistry. The study of non-covalent interactions is crucial to understanding many biological processes that rely on these forces for structure and function. Biological systems are often the inspiration for supramolecular research. However, novel supramolecular structures are related to novel intermolecular relationships in many ways that are additional to the chemistry of the molecular structures itself. So although atoms play a critical role in the paradigms of chemistry, it is molecular structure of a chemical that is central to the chemistry of many important technological and biological materials. The "intellectual glue" of a molecular structure is the covalent bond, the connectivity of atoms, and the stereochemistry of atoms in space that are associated with covalent bonds. The paradigm of the covalent chemical bond provides the many rules governing the structures, dynamics, physical characteristics, and chemical transformations of molecules.

The level of atomic structure is an inadequate foundation for a sufficient understanding aspects of chemistry where molecular aspects dominate. The level of molecular structure is inadequate for understanding aspects of chemistry where supramolecular aspects dominate. In supramolecular systems, the chemistry of the intermolecular bond binds molecules together into assemblies we can term supermolecules. In supramolecular systems, noncovalent intermolecular bonds are more far varied and complex than covalent intramolecular bonds in the structures known as molecules. Supramolecular systems can be held together by much weaker forces than the atoms in a molecule. For example, forces holding several molecules together as supramolecular structures can include dispersion forces, hydrogen bonds, and hydrophobic bonds. These forces per atom contact may be small, however the opportunity for and then presence of multiple weak bonds can occur according to principles of cooperativity interactions, so as to enhance the energetic stability of a supramolecular structure. However, the cooperative interactions are readily reversible because each "bonding contact" is relatively weak. This creates a variable supramolecular structure flexibility and varying combinations of molecular connections and stereochemical conformational relationships. In other words, supramolecular systems can engage in supervalency states in which supramolecular complexes comprising many individual molecules are stable into a number of combinations with overall conformations at both molecular and supramolecular levels due to the possible summation of various combinations of a large number of weak intermolecular bonds. Remarkable examples of this are micelles and the double helix of DNA.

In one of its most important forms, supramolecular chemistry is concerned with the structure and dynamics of a small molecule (termed a guest) that is noncovalently bound to a larger molecule (termed a host). The symbol guest/host has its greatest chemical informational value when the distinction between the guest and host is clear. In many guest/host complexes, the guest is a molecule that is relatively small compared with the host and the host may either be a single large molecule or an assembly of molecules that behave as a unit. Typically, the host provides a cage that completely surrounds the guest (guest/cage) or the host provides a cavity (guest/cavity) that partially surrounds the guest. However, there are also examples for which the notion of guest and host are blurred. For example, in a micelle composed of surfactant monomers, a single monomer may be considered as a guest in a host in its own supramolecular assembly. In turn, a molecule that is not a monomer surfactant is a clear-cut guest in the micelle assembly of surfactants.

A useful term for the formation of an intermolecular bond between guest and host is "complexation," a term that preserves the idea of chemically relevant "looseness" expected of noncovalent bonds between molecules. In this regard, the host is the partner of the guest/host complex whose property design and structural variations determine the types of guests that will be bound in the complex. The other partner, the complexed guest, is usually the partner whose chemistry or physical properties are being investigated. These concepts are derived from the paradigms of enzyme chemistry and provide a familiar and useful working basis for the discussion of supramolecular chemistry. A guest/host complex may be considered as a supermolecule or supramolecular assembly depending on the complexity of the supramolecular structure under discussion.

Supramolecular Chemistry: Structure and Dynamics at the Topological, Geometric, and Chemical Level Supramolecular chemistry has been defined in various ways such as the chemistry of molecular assemblies and the intermolecular bond, chemistry beyond the molecule, and chemistry of the noncovalent bond. Each definition, though important, have their limitations and exceptions. Indeed, supramolecular chemistry can be defined to encompass the chemistry of molecular assemblies from a molecule in a molecular solvent cage to the constellation of molecular assemblies (composed of proteins, lipids, DNA, RNA, etc.) that constitute the enormous chemical complexity of a living cell.

Because the bonding between molecules in guest/host complexes is often a mixture of many weak electrostatic and dispersion interactions, it is difficult to define and classify the nature of the noncovalent bonds precisely. As a starting point for discussing supramolecular assemblies it is convenient to consider the "neighborhood" relationships between certain atoms of the guest with those of the host that can control the physical and chemical properties of the guest/host complex. Often it is the properties of the guest that are most significantly modified by neighborhood relations imposed by binding to the host of interest, but the combined supramolecular properties of the complex and modification of the host structure are also of considerable interest and importance.

By neighborhood relationships in supramolecular chemistry we mean that two molecules are in the proximity of one another during a certain time period. During this time period the two molecules may be considered to be bonded irrespective of the nature of the bonding and the reason the atoms are close to one another. For example, a molecule that is contained as a guest inside a host fullerene has a clear neighborhood relationship to the internal cage of the fullerene. Similarly, a molecule that is contained as a guest in the cavity of a host such as a cyclodextrin or a cavitand has a clear neighborhood relationship to the cavity of the host. A molecule that is contained as a guest in a crystal and is surrounded by molecules of a crystalline host has a clear neighborhood relationship to the surrounding molecules of the crystal. Finally, a guest molecule that is intercalated in a host DNA double-helix has a chemical relationship to a small set of specific bases that are in its neighborhood.

Nanoparticle therapeutics are typically particles comprised of therapeutic entities, such as small-molecule drugs, peptides, proteins and nucleic acids, and components that assemble with the other therapeutic entities, such as lipids and polymers. Such nanoparticles can have enhanced anti-cancer effects compared with the therapeutic entities they contain. This is owing to more specific targeting to tumor tissues via improved pharmacokinetics and pharmacodynamics, as well as active intracellular delivery. These properties depend on the size and surface properties, including the presence of targeting ligands, of the nanoparticle. A limited number of nanoparticle systems have achieved clinical applications, and information is becoming available to begin to understand some of the issues of moving these experimental systems into humans. Although an enormous amount of research is ongoing into nanoparticle discovery and development, only a small number of nanoparticle products may become clinically useful. For example, it is known that immuno-stimulatory components of nanoparticles are difficult to manufacture on a large-scale by good manufacturing practices (GMP) and there are enormous difficulties in using assays to evaluate their chemistry, manufacturing and quality.

Nevertheless, significant effort has been devoted to explore uses of nanoparticles in biology and medicine and a few kinds of nanoparticles have been tested pre-clinically in animals, used in clinic trials, and some are now used clinically (Davis et al., Nat. Rev. Drug Discov. 2008, vol. 7, p. 771) Examples of kinds of nanoparticles include gold nanoshells (Loo et al., Technol. Cancer Res. Trea, vol. 3, p. 33, 2004), quantum dots (Gao et al., Nat. Biotechnol., vol. 22, p. 969, 2004; Nie et al., Annu. Rev. Biomed. Eng., vol. 9, p. 257, 2007) and super-paramagnetic nanoparticles, (Jun et al., Angew. Chem., vol. 120, p. 5200, 20080; Jun et al., Angew. Chem. Int. Ed., vol. 47, p. 5122, 2008). Nanoparticles carrying target-specific ligands are used for in vivo cancer imaging, and drug molecules can be packaged into polymer-based nanoparticles or liposomes (Heath et al., Annu. Rev. Med., vol. 59, p. 251, 2008; Torchilin et al., Nat. Rev. Drug Discov., vol. 4, p. 145, 2005) for controlled drug release (Napier et al., Poly. Rev., vol. 47, p. 321, 2007; Gratton et al., Acc. Chem. Res., vol. 41, p. 1685, 2008). Positive charge nanoparticles have been used as a non-viral delivery system in vitro and in vivo for genetic manipulation and genetic programming (Davis et al., Nat. Rev. Drug Discov., vol. 7, p. 771, 2008; Green et al., Acc. Chem. Res., vol. 41, p. 749, 2008; Pack et al., Nat. Rev. Drug Discov., vol. 4, p. 581, 2005).

There is a need for a development of alternative synthetic processes so that new kinds of nanoparticles can become available which have improved properties including: (i) a better-controlled size, (ii) an improved morphology, (iii) a lower toxicity, (iv) a lower immune system side-effect, (v) a more selectable in vivo rate of degradation, (vi) a more physiological surface charge, (vii) an improved chemio-physiologic stability, (viii) a slower rate of metabolism, and (ix) a slower rate of elimination from a person after their administration to the person.

Noble-metal nanostructures with unique photophysical properties have been given a lot of attention as photothermal agents to treat cancer (Anderson et al., Science, vol. 220, p. 524, 1983; Jain et al., Acc Chem Res, vol. 41, p. 1578, 2008; An et al., Nano Today, vol. 4, p. 359, 2009; Lal et al., Acc Chem Res, vol. 41, p. 1842, 2008). Nanostructure photo-thermal properties are modified by their size and shape (Lal et al., Acc Chem Res, vol. 41, p. 1842, 2008; Skrabalak et al., Acc Chem Res, vol. 41, p. 1587, 2008). In particular, photothermal gold (Au) nanostructures are well known (Lapotko et al., Laser Surg Medi, vol. 38, p. 631, 2006; Huang et al., Lasers Med Sci, vol. 23, p. 217, 2008), nanoshells (Gobin et al., Nano Lett, vol. 7, p. 1929, 2007; Hu et al., J Am Chem Soc, vol. 131, p. 14186, 2009; Kim et al., Angewandte Chemie-International Edition, vol. 45, p. 7754, 2006), nanorods (Dickerson et al., Cancer Letters, vol. 269, p. 57, 2008; Huang et al., Langmuir, vol. 24, p. 11860, 2008) and nanocages (Skrabalak et al., Acc Chem Res, vol. 41, p. 1587, 2008; Chen et al., Nano Lett, vol. 7, p. 1318, 2007; Au et al., ACS Nano, vol. 2, p. 1645, 2008). Au nanostructures are an improvement over the low light absorption and undesired photo-bleaching of organic dye photothermal agents (Huang et al., Lasers Med Sci, vol. 23, p. 217, 2008). It is a disadvantage that nanostructure-based agents need short-wave length light (in the range of tens to hundreds nanometers) to kill cancer cells (Lowery et al., Clin Cancer Res, vol. 11, p. 9097s, 2005). In addition, the known nanostructure-based agents are not well eliminated from liver, spleen and kidney), and this accumulation is not desirable for a medical treatment (Mitragotri et al., Nat Mater, vol. 8, p. 15, 2009; Choi et al., Nat Biotechnol, vol. 25, p. 1165, 2007; Nel et al., Nat Mater, vol. 8, p. 543, 2009). To help reduce this problem, photophysical properties of metal nano structures is improved by modifications that cause them to self-aggregate (Khlebtsov et al., Nanotechnology, vol. 17, p. 5167, 2006; Lu et al., J Mater Chem, vol. 19, p. 4597, 2009; Zhuang et al., Angew Chem Int Ed Engl, vol. 47, p. 2208, 2008; Troutman et al., Adv Mater, vol. 20, p. 2604, 2008; Ofir et al., Chem Soc Rev, vol. 37, p. 1814, 2008; Elghanian et al., Science, vol. 277, p. 1078, 1997; Lin et al., Adv Mater, vol. 17, p. 2553, 2005; Katz et al., Angew Chem Int Ed Engl, vol. 43, p. 6042, 2004; Cheng et al., Nature Nanotechnology, vol. 3, p. 682, 2008; Maye et al., J Am Chem Soc, vol. 127, p. 1519, 2005; Niemeyer, Angewandte Chemie-International Edition, vol. 40, p. 4128, 2001; Klajn et al., Nat Chem, vol. 1, p. 733, 2009). Notably, Lapotko (Cancer Lett, vol. 239, p. 36, 2006) enhanced photothermal of gold nanoparticles by aggregating the gold nanoparticles using antibodies on cell membranes and inside cells (Govorov et al., Nano Today, vol. 2, p. 30, 2007; Richardson et al., Nano Lett, vol. 9, p. 1139, 2009). Self-assembly of small metal building blocks as colloids (Mitragotri et al., Nat. Mater., vol. 8, p. 15, 2009; Choi et al., Nat Biotechnol, vol. 25, p. 1165, 2007; Nel et al., Nat Mater, vol. 8, p. 543, 2009) improves their renal clearance and makes a better photothermal agent.

Needed are non-viral methods for delivery of gene therapy that can (i) carry and protect genetic materials, e.g., DNA and siRNA, and (ii) delivery the gene therapy to selected cells cells and tissue types (Kim et al. Nat Rev Genet, vol. 8, p.p. 173-184, 2007). Improvements in non-viral gene delivery vehicles have been made (Glover et al., Nat Rev Genet, vol. 6, pp. 299-310, 2005; Rosi et al., Chem. Rev., vol. 105, pp. 1547-1562, 2005). Non-viral gene delivery systems prior art includes (Niidome et al., Gene Ther., vol. 9, p. 1647-1652, 2002; Prata et al., Chem. Commun., pp. 1566-1568, 2008; Woodrow et al., Nat. Mater., vol. 8, pp. 526-533, 2009; Chen et al., Chem. Commun., pp. 4106-4108, 2009; Torchilin et al., Proc Natl Acad Sci USA, vol. 100, pp. 1972-1977, 2003). Nanoparticle-based gene delivery vehicle prior art includes (Liang et al., Proc Natl Acad Sci USA, vol. 102, pp. 11173-11178, 2005; Kumar et al., Chem. Commun., pp. 5433-5435, 2009; Bazin et al., Chem. Commun., pp. 5004-5006, 2008; Cheon et al., Acc. Chem. Res., vol. 41, pp. 1630-1640, 2008).

Although nanoparticles are promising non-viral transfection agents for effective and safe delivery of nucleic acids into specific type of cells or tissues, the problems with their manufacture and use include their (1) slow, multistep synthetic approaches, and (2) restricted diversity of delivery materials. These problems are a major obstacle to achieving optimal transfection performance. Thus, needed are methods of quicker and more efficient methods of manufacture which can employ a variety of delivery materials.

BRIEF SUMMARY OF THE INVENTION

Supramolecular nanoparticles may comprise: a combination of nanostructures selected from the group consisting of combinatorial carboxylated cobalamins obtained from a first combinatorial synthesis; combinatorial carboxylated dipyridamoles obtained from a second combinatorial synthesis; basic amino acid polypeptides obtained from a third combinatorial synthesis, and any combination thereof.

The supramolecular nanoparticles may have antiviral properties, and may further comprise dynamic self-organizing soluble nanostructures, and the nanostructures may further comprise a plurality of binding components; a plurality of organic cores; and a plurality of terminating components.

The supramolecular nanoparticles may have one of the binding components which may further comprise combinatorial carboxylated cobalamins which may have a number of binding regions, and the organic cores may further comprise the combinatorial carboxylated dipyridamoles which may have at least one binding element adapted for binding to the combinatorial carboxylated cobalamins, and the organic cores may further comprise mechanical structures for the dynamic self-organizing soluble nanostructures, and the binding of the combinatorial carboxylated cobalamins to the combinatorial carboxylated dipyridamoles may further comprise first inclusion complexes.

The supramolecular nanoparticles may have terminating components which may each have at least one terminating binding element that binds to a remaining binding region of one of the binding components and as such may further comprise second inclusion complexes.

The supramolecular nanoparticles may have basic amino acid polypeptides which may further comprise carboxylated basic amino acids of basic amino acids selected from the group consisting of lysine, histidine, arginine, derivatized lysine, derivatized histidine, derivatized arginine, acylated lysine, acylated histidine, acylated arginine, and any combination thereof.

The supramolecular nanoparticles may have a plurality of terminating components which may occupy the remaining binding regions of the plurality of binding components, and the plurality of terminating components may be in a quantity relative to the plurality of the binding regions of the plurality of the binding components which may terminate further binding of binding components, and the supramolecular nanoparticles may further comprise discrete nanoparticles based on the dynamic self-organizing soluble nanostructures.

The supramolecular nanoparticles may have combinatorial carboxylated cobalamins which may be a succinylated cyanocobalamins mixture.

The supramolecular nanoparticles may have combinatorial carboxylated cobalamins which may be a succinylated methyl cobalamins mixture.

The supramolecular nanoparticles may have combinatorial carboxylated cobalamins which may be a succinylated hydroxycobalamins mixture.

The supramolecular nanoparticles may have combinatorial carboxylated cobalamins which may be a succinylated cobamides mixture.

The supramolecular nanoparticles may have combinatorial carboxylated cobalamins which may be selected from the group consisting of succinylated hydroxycobalamins mixtures, succinylated cobamides mixtures, succinylated hydroxycobalamins mixtures, succinylated methyl cobalamins mixtures, succinylated cyanocobalamins mixtures, and any combination thereof.

The supramolecular nanoparticles may have at least one of the organic cores which may further comprise at least one element selected from a photo-dynamic component which may be supramolecular combinatorial carboxylated riboflavins.

The supramolecular nanoparticles may have supramolecular combinatorial carboxylated riboflavins which may be supramolecular combinatorial succinylated riboflavins.

The supramolecular nanoparticles may have supramolecular combinatorial carboxylated riboflavins which may be supramolecular combinatorial succinylated flavin mononucleotides.

The supramolecular nanoparticles may have supramolecular combinatorial carboxylated riboflavins which may be supramolecular combinatorial succinylated flavin dinucleotides.

The supramolecular nanoparticles may have combinatorial carboxylated dipyridamoles which may be supramolecular succinylated combinatorial dipyridamoles.

The supramolecular nanoparticles may have combinatorial carboxylated dipyridamoles which may be supramolecular maleylated combinatorial dipyridamoles.

The supramolecular nanoparticles may have combinatorial carboxylated dipyridamoles which may be supramolecular carboxymethylated combinatorial dipyridamoles.

The supramolecular nanoparticles may have carboxylated basic amino acids which may be selected from the group consisting of succinylated lysine, succinylated histidine, succinylated arginine, and any combination thereof.

The supramolecular nanoparticles may have carboxylated basic amino acids which may be selected from the group consisting of maleylated lysine, maleylated histidine, maleylated arginine, and any combination thereof.

The supramolecular nanoparticles may have carboxylated basic amino acids which may be selected from the group consisting of carboxymethylated lysine, carboxymethylated histidine, carboxymethylated arginine, and any combination thereof.

The supramolecular nanoparticles may have carboxylated basic amino acids which may be selected from the group consisting of carboxymethylated lysine, carboxymethylated histidine, carboxymethylated arginine, succinylated lysine, succinylated histidine, succinylated arginine, maleylated lysine, maleylated histidine, maleylated arginine, and any combination thereof.

The supramolecular nanoparticles may have a plurality of the terminating components which may comprise at least one terminating component selected from the group consisting of a polyethylene glycol, a polymer, a polypeptide, a oligosaccharide, and any combination thereof.

The supramolecular nanoparticles may have organic cores which may comprise at least one organic core selected from the group consisting of a dendrimer, a branched polyethyleneimine, a linear polyethyleneimine, a polylysine, a polylactide, a poly-lactide-co-glycoside, a polyanhydride, a poly-ε-caprolactone, a polymethyl methacrylate, a poly (N-isopropyl acrylamide), and a polypeptide, and any combination thereof.

The supramolecular nanoparticles may have at least one of the plurality of the binding components which may further comprises combinatorial carboxylated derivatives of the basic oligopeptide KKRKRKRKR.

The supramolecular nanoparticles may have combinatorial carboxylated derivatives of the basic oligopeptide KKRKRKRKR which may be derivatives which may be succinylated on between 1 to 9 of the free amino group residues of the basic oligopeptide KKRKRKRKR.

The supramolecular nanoparticles may have combinatorial carboxylated derivatives of basic oligopeptide KKRKRKRKR which may be derivatives which may be maleylated on between 1 to 9 of the free amino group residues of the basic oligopeptide KKRKRKRKR.

The supramolecular nanoparticles may have combinatorial carboxylated derivatives of basic oligopeptide KKRKRKRKR which may be derivatives which may be carboxymethylated on between 1 to 9 of the free amino group residues of the basic oligopeptide KKRKRKRKR.

The supramolecular nanoparticles may have combinatorial carboxylated derivatives of basic oligopeptide KKRKRKRKR which may be derivatives which may be combinatorial mixtures which are succinylated, maleylated and carboxymethylated on between 1 to 9 of the free amino group residues of the basic oligopeptide KKRKRKRKR The supramolecular nanoparticles may have a binding component which is poly-L-lysine.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
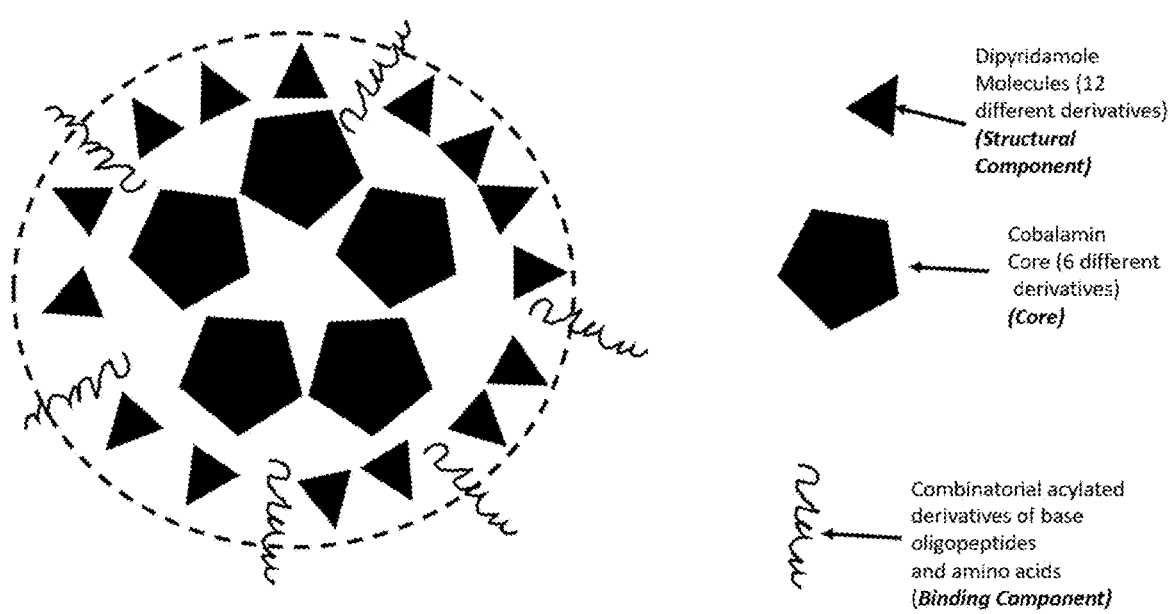
FIG. 1 depicts structures of a soluble self-assembled nanoparticle, a dynamic combinatorial cobalamide likecore, a dynamic combinatorial dipyridamole like-structural component, dynamic combinatorial derivatives of base oligopeptides, and amino acids like-binding component.

In general, embodiments of the invention relate to supramolecular structures, also termed a supramolecular nanoparticle (SNP) that can be prepared using molecular recognition properties of building blocks based on dynamic quasi-living self-assembling system. The invention embodiments also include methods of producing supramolecular structures using molecular recognition and using methods of controlling the size of the nanoparticles produced. The invention embodiments also include methods of using the supramolecular structures for treating viral infections.

In some general embodiments of the invention, the supramolecular nanoparticle (SNP) comprises:
a) a plurality of binding components,
   wherein each binding component has a plurality of binding regions, and
   wherein the plurality of binding regions comprise combinatorial carboxylated cobalamins;
b) a plurality of cores for providing a mechanical structure for a self-assembly of a supramolecular soluble system,
   wherein the plurality of the cores is an organic core which comprises a core binding element for binding to the plurality of the binding regions so as to form a first inclusion complex,
   wherein the core binding element comprises combinatorial carboxylated dipyridamole, and
   wherein the first inclusion complex is the combinatorial carboxylated cobalamin with the combinatorial carboxylated dipyridamole; and
c) a plurality of terminating components with each terminating component having a single terminating binding element for binding to remaining binding regions of one of the plurality of the binding components so as to form a second inclusion complex,
   wherein the single terminating binding element comprises combinatorial carboxylated dipyridamole,
   wherein the second inclusion complex is the combinatorial carboxylated dipyridamole,
   wherein the plurality of the cores and the plurality of the binding components are self-assembled carboxylated basic amino acids selected from the group consisting of lysine, histidine, arginine, and any combination therefor and the carboxylated basic amino acids self-assemble when brought into contact so as to form self-assembled supramolecular soluble systems,
   wherein the plurality of the terminating components act to occupy the remaining binding regions of the plurality of the binding components, and
   wherein the plurality of terminating components are present in a sufficient quantity relative to quantity of the plurality of the binding regions with the plurality of the binding components so as to terminate further binding, so as to form a discrete particle.

Structural Component

In some embodiments of the present invention, the structural component has a plurality of binding elements that bind to the binding regions of the binding components. The binding element is a chemical moiety that binds to the binding region of the binding component by one or more intermolecular forces. The binding element of the structural component and the binding region of the binding element are specifically selected to bind to each other and may use molecular recognition properties to identify the binding regions. For example, a binding region may comprise a combinatorial carboxylated cobalamin, or a carboxylated cobalamine or a cobalamine derivative.

In some embodiments of the present invention, the structural component is at least an inorganic or organic core.

FIG. 1 depicts invention embodiment structures of a soluble self-assembled nanoparticle, a dynamic combinatorial cobalamide like core, a dynamic combinatorial dipyridamole like structural component, dynamic combinatorial derivatives of base oligopeptides, and amino acids like binding component. In some embodiments the cores are cobalamine self-assembled structures which have an inorganic cores selected from the group consisting of an inorganic nanoparticle, a metal nanoparticle, a gold nanoparticle, a silver nanoparticle, a silicon nanoparticle, a nanoparticle of a metal, a nanoparticle of an element, a metal oxide nanoparticle, and any combination of nanoparticles thereof. For example, inorganic nanoparticles include metal oxide nanoparticles (e.g. silica nanoparticles or iron oxide nanoparticles), and nanoparticles of other inorganic compounds. Functional nanoparticles may be used, such as, magnetic nanoparticles, quantum dots (e.g., CdS or CdSe nanoparticles), or semi conductive oxide particles.

An inorganic core can have a shape selected from the group consisting of spherical, triangular, cubic, star-like, rod-like, shell, diamond-like, plate-like, pyramidal, irregular, cage structure, and a combination thereof.

Inorganic nanoparticles are known in the art. The inorganic core can bind to binding regions of the binding component. In some embodiments, the binding component has binding regions that can bind to the inorganic core directly. In other embodiments of the present inventions, a surface of the inorganic core has been derivatized with a plurality of binding elements so as to be capable of binding to a plurality of binding element regions of the binding component by one or more intermolecular forces.

In some embodiments of the present invention, a plurality of inorganic core particles can be present in the supramolecular structure. In such cases, a plurality of the inorganic core particles may bind to a plurality of the binding components so as to form a crosslinked network or a hydrogel. The continuous propagation of a crosslinked network may be constrained or terminated as desired by using a terminating component(s) that also can bind to a binding region(s) of the binding component(s).

In some embodiments, the structural component is an organic core. Organic cores may include organic cores selected from the group consisting of combinatorial self-assembled cobalamine derivatives, dendrimers, polymers, proteins, oligosaccharides, micelles, liposomes, vesicles, and a combination thereof. For example, in some cases, the organic core may be a dendrimer, polymer or polypeptide. A structural component includes a structural core selected from the group consisting of a dendrimer, a polyamidoamine dendrimer (PAMAM), a branched polyethyleneimine (PEI), a linear polyethyleneimine, a polylysine, a polylactide, a polylactide-co-glycoside, a polyanhydride, a poly-ε-caprolactone, a polymethyl methacrylate, a poly (N-isopropyl acrylamide), a polypeptide, and a combination thereof. In some embodiments, the organic core is a polyamidoamine dendrimer or a poly-L-lysine polymer.

In some embodiments, the binding regions of the binding component bind to binding elements which may be present as part of the organic core structure. In other embodiments, the organic core is derivatized with a plurality of binding elements such as for example, combinatorial self-assembled dipyridamole derivatives. The binding elements can bind to the binding regions of the binding component by one or more intermolecular forces and self-assemble into a crosslinked network or hydrogel. A continuous propagation of the crosslinked network may be constrained or terminated by a terminating component(s) that also may bind to a binding region(s) of a binding component(s). The binding element(s) and binding region(s) may be selected based on the type of binding(s) selected and may use/have molecular recognition properties in some cases.

Figure 2:
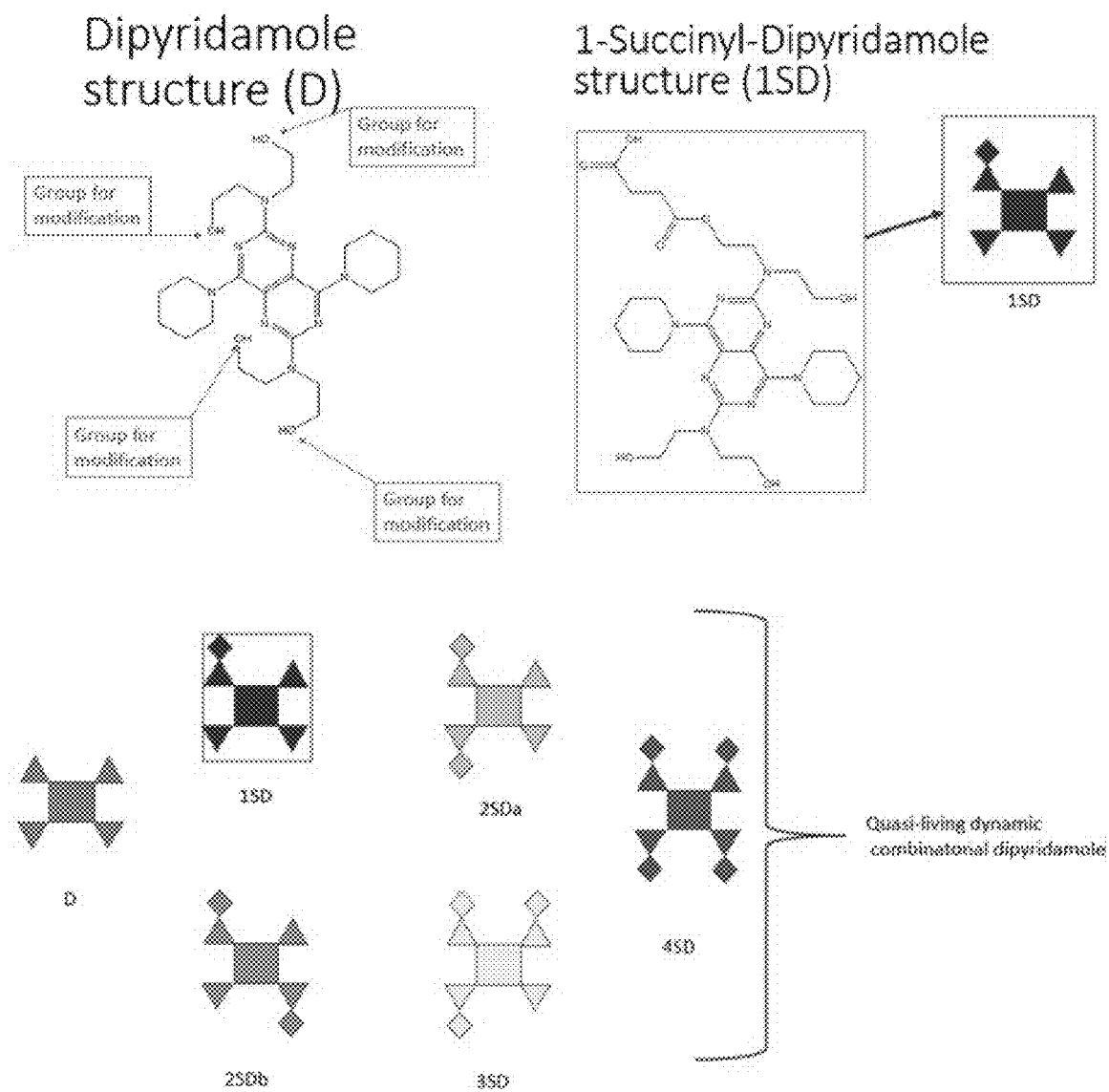
FIG. 2 depicts self-assembled, dynamic combinatorial derivatives of dipyridamole and principal(s) of their synthesis.

FIG. 2 depicts invention embodiment self-assembled combinatorial dynamic derivatives of dipyridamole and principle of their synthesis. Numerous dendrimers are known in the art. The advantage of dendrimer cores lies in their rapid synthesis, and easy ability to be functionalized with binding elements. In some embodiments of the present invention, the dendrimer may be synthesized to include binding elements as part of the structure. Alternatively, in other embodiments during dendrimer synthesis, a reactive functionality may be present at each terminating point, which may be terminated with a chemical moiety that functions as a binding element to bind to the binding region of the binding component. Examples of specific dendrimers useful for invention embodiments include polyamidoamine dendrimer (PAMAM).

Many polymers are known in the art. The advantage of using a polymer cores lies in its rapid synthesis and its ability to be easily functionalized with a binding element(s). In some embodiments of the present invention, the polymer may be synthesized to include binding elements as part of the polymer structure. Alternatively, in other embodiments, reactive functional groups on a polymer may be derivatized with a chemical moiety(s) that function(s) as a binding element(s). For example, a polypeptide(s) having a lysine residue(s) with a reactive amine ($NH_2$) group(s) which may be functionalized with a binding element(s). One polypeptide example is poly-L-lysine.

In some embodiments, two or more different structural components are present, in which case each structural component may have binding elements for binding to a binding component(s).

In some embodiments of the present invention, the structural component can be a polyamidoamine dendrimer derivatized with a binding element(s), such as an oligopeptide KKRKRKRKR and related combinatorial self-assembled carboxylated derivative(s). Note: K is the single letter amino acid symbol for lysine. Note: R is the single letter amino acid symbol for arginine. In some embodiments of the present invention, the structural component may also be an inorganic nanoparticle derivatized with adamantine such as a metal nanoparticle derivatized with adamantine, or metal oxide nanoparticle derivatized with adamantine, more specifically for example, a gold nanoparticle derivatized with adamantine.

Terminating Component

In some embodiments of the present invention, the terminating components occupy binding regions of the binding components to constrain the continuous propagation of the crosslinked network when the terminating components are present in a sufficient quantity relative to the binding regions of the binding components. The binding component and structural component can self-assemble into a supramolecular structure, while the terminating components can occupy binding regions and prevent further self-assembly between the binding component and structural component. For some embodiments of the present invention, the extent to which the terminating component limits the self-assembly process is based on the relative concentration between the binding elements on the terminating components and the number of binding regions on the binding components. For some invention embodiments, when the concentration of terminating components reaches a sufficient level, then a self-assembly of the three components: (1) structural component(s), (2) binding component(s), and (3) terminating component(s) results in formation of a particle (a nanoparticle), rather than a crosslinked network or hydrogel. A benefit of this supramolecular approach to producing a nanosized particle(s) is that the size of the final particles (nanoparticles) may be readily adjusted by changing the relative concentrations of the components in the preparation mixture.

In some embodiments, the terminating component has a single binding element that binds to one of the binding regions on the binding component. In these cases, each terminating component has only one binding element. The binding element is a chemical moiety that binds to the binding region of the binding component by one or more intermolecular forces. These terminating components bind to only one binding region on the binding component. In this way, crosslinking between the terminating component and the binding component may be avoided.

The terminating component can be a polymer, polypeptide, oligosaccharide or small molecule, so long as the terminating component binds to a binding region of the binding component. In some embodiments, the terminating component is a polymer that is derivatized with a binding element. In others, the terminating component is poly (ethylene glycol) derivatized with a binding element, such as reside of maleic acid.

The supramolecular structure may have two or more terminating components. In these scenarios, the supramolecular structure may have 2, 3, 4, 5, or 6 different terminating components. Each terminating component may have the same binding element, or they may have different binding elements, but each binding element will bind to the binding region of the binding component.

Binding Component

The binding component has a plurality of binding regions that bind to the structural component and the terminating component may include a terminating component selected from the group consisting of an unmodified cobalamine, a dipyridamole, basic amino acids, unmodified peptide such as KKRKRKRKR, and any combination thereof. The binding region is a chemical moiety that binds to the structural component and the terminating component by one or more intermolecular forces.

In some embodiments, two or more different binding components may be used, so long as both have binding regions that bind to the structural and terminating components.

The binding component can be a polymer, oligosaccharide, or polypeptide. Any suitable material may be used that includes a plurality of binding regions. The binding component can also be polyethylene imine or branched polyethylene imine derivatized with a plurality of binding regions. A specific example of a binding component is a branched polyethylene imine derivatized with β-cyclodextrin. Another example of a binding component is poly-L-lysine derivatized with β-cyclodextrin.

Molecular Recognition

In some embodiments of the present invention, the binding regions and/or binding elements are molecular recognition elements. In other words, a binding region forms a molecular recognition pair with a binding element on either the structural component or the terminating component.

Figure 3:
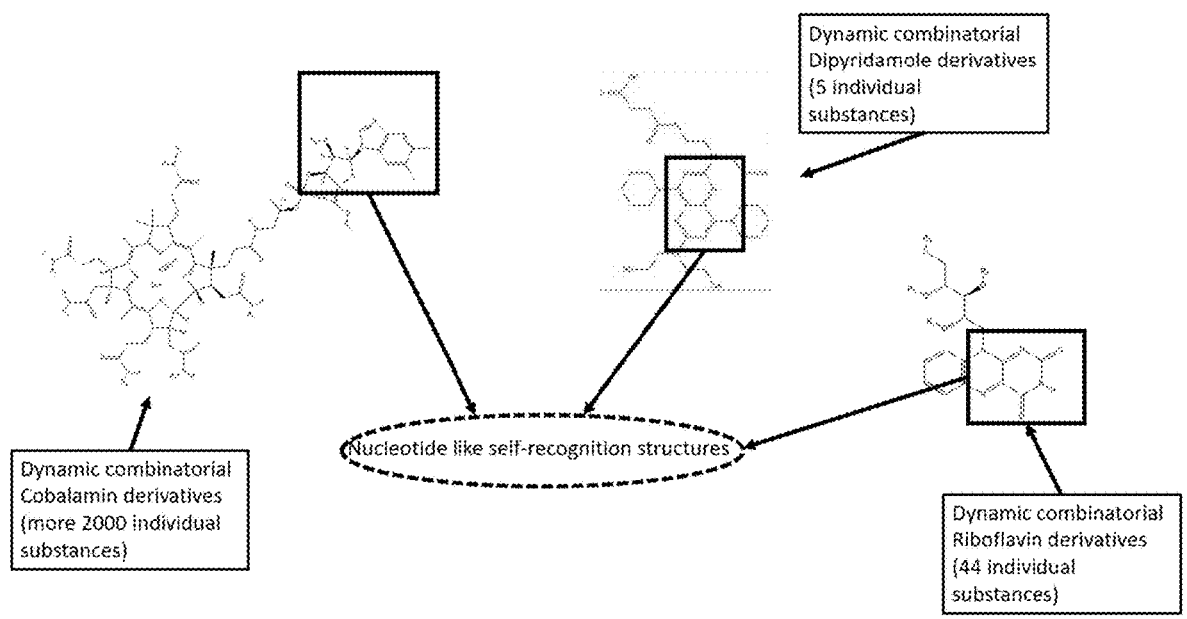
FIG. 3 depicts a principal of molecular recognition between different substances on base nucleotide-like structures.

FIG. 3 depicts a principle of molecular recognition between different substances on base nucleotide-like structures that has an important utility in some present invention embodiments. Molecular recognition refers to the specific interaction between two or more molecules through one or more intermolecular forces. The molecules involved in molecular recognition exhibit molecular complementarity and are called a molecular recognition pair or host-guest complex. In this case, the terms "host" and "guest" do not impart any particular relationship, but only describe two compounds which exhibit molecular complementarity, i.e., bind to each other by molecular recognition. A "host" and a "guest" bind to each other, while two "host" compounds do not. Molecular recognition is a specific interaction, meaning that each molecular recognition element will bind to complementary molecules having particular structural features. In general, molecular recognition pairs bind more tightly than non-specific binding, since multiple interactions occur between the two molecular recognition elements.

Invention embodiment examples of molecular recognition pairs include small molecule host-guest complexes (including but not limited inclusion complexes), pairs of complementary oligonucleotide sequences (e.g. DNA-DNA, DNA-RNA or RNA-RNA that bind to each other by hybridization), antibody-antigen, protein-substrate, protein-inhibitor, and protein-protein interactions (such as α-helical peptide chains and β-sheet peptide chains).

In some embodiments, the supramolecular structure self-assembles by molecular recognition. In this case, binding regions on the binding component form a molecular recognition pair with binding elements on the structural component. Binding elements on the terminating component also bind to binding regions on the binding component to form a molecular recognition pair. The molecular recognition pairs formed between the binding component and the structural component may be the same as the molecular recognition pair formed between the binding component and the terminating component, or they may be different. In other words, in some embodiments the binding element on the structural component may be the same as the binding element on the terminating component, or they may be different, but both binding elements bind to the same binding region on the binding component.

For the present invention, molecular recognition pairs include molecular recognition pairs, combinations of molecular recognition pairs, and sets of multiple molecular recognition pairs. Some example embodiments of molecular recognition pairs may be selected from the group consisting of a adamantane-β-cyclodextrin complex, a diazobenzene-α-cyclodextrin complex, a steroid-based molecular recognition pair, a pyrene-based molecular recognition pair, a steroid, a pyrene, a Rhodamine in a cylodextrin, a doxorubicin in a cyclodextrin, a biotin-streptavidin, a complementary pair of nucleotide bases, a complementary pair of nucleotides, a complementary pair of oligonucleotides, and a combination thereof.

Functional Elements

In some embodiments of the present invention, at least one of the structural components, binding components or terminating components includes a functional element. A functional element may be a chemical moiety that imparts an additional function or activity to the supramolecular structure that is not present when the functional element is missing. The functional element can be a light emitting (i.e. fluorescent or phosphorescent) compound like combinatorial self-assembling riboflavin derivatives. Fluorescent and phosphorescent labeled supramolecular structures may be used, for example in imaging studies in vitro or in vivo. For example, riboflavin is fluorescent under UV light and may be used as a functional element. The functional element may also be a compound having a radioactive or magnetically active isotope. For example, positron emitting isotopes, such as $^{64}$Cu may be used to measure biodistribution of the supramolecular structures. Other useful suitable isotopes would be readily apparent to one of ordinary skill.

Figure 4:
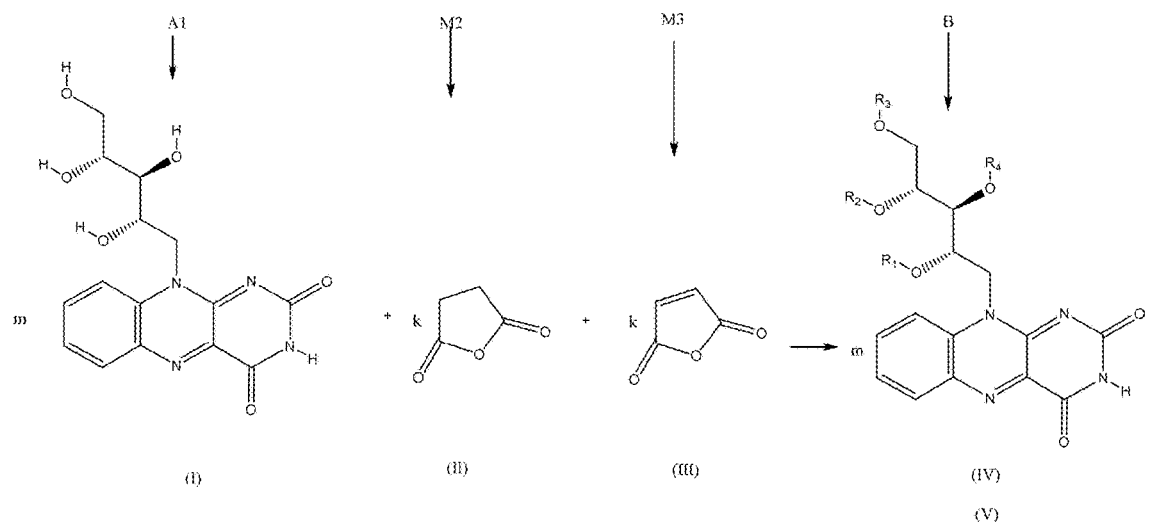
FIG. 4 depicts a synthesis scheme for dynamic riboflavin (IV) with 44 components on mixture that react one with other, and with a formula for calculating the combinatorial synthesis of a fully substituted derivative thereof, wherein m=1, k=4, and wherein modifier (II) is tetra-succinyl riboflavin (V).

FIG. 4. depicts a synthesis scheme for a functional element as an example of the present invention, wherein the functional element is dynamic riboflavin (IV) with 44 components on mixture that react one with other, and with a formula for calculating the combinatorial synthesis of a fully substituted derivative thereof, wherein m=1, k=4, and modifier (II) is tetra succinyl-riboflavin (V). In some invention embodiments, a functional element may be a targeting element that functions to target the supramolecular structure to particular cells. Such targeting functional elements include peptides, oligonucleotides, antibodies, and small molecules that bind to cell surface proteins. In general, any chemical moiety that specifically binds to one or more cell surface protein may be incorporated into the supramolecular structure to serve as a functional element. The cell surface proteins may be, for example, a protein on a cancer cell or on a bacterium or fungi. Specific examples of functional elements which are cell targeting moieties for the present invention include RGD and EGF, folic acid, transferrin, and include antibodies for targeting cell surface markers such as for example Herceptin for Her2 on breast cancer cells.

A functional element may be selected for the present invention which is a cell permeation functional element that functions to increase cell membrane permeation. Specific examples of ligands that increase cell membrane permeation include the TAT ligand. Various other cell membrane permeation ligands may also be used in some embodiments of the present invention.

In some embodiments of the present invention, the supramolecular structure can have two or more functional elements. For example, the supramolecular structure may have two targeting functional elements as a means for synergistically increasing cell targeting selectivity, or as a means for increasing binding affinity by the multiple functional elements serving for targeting more than one cell surface protein on a biological cell. A cell means a biological cell. Other examples of multiple functional elements include supramolecular structures having a targeting functional element and having a cell permeation functional element, as a means for a synergistic combining of the effects of improved cell targeting and increased cell permeation. Yet another example of multiple functional elements in a supramolecular structure for providing a synergy means would be to make and use a supramolecular structure having (1) an imaging functional element which is light-emitting or a radioisotope functional element and (2) a targeting functional element for imaging targeted cells. Present invention embodiments include using functional elements combinations such as using two targeting functional elements and a cell permeation functional element, such as using two targeting functional elements and a visualizing functional element, and the using of like combinations of functional elements.

In some embodiments of the present invention, the supramolecular structure includes two or more terminating components, each of which may further include a functional element. In this way, multiple functional elements may be incorporated by using multiple terminating components. For example, a supramolecular structure may have (1) a terminating component having no functional element and (2) a terminating component having a targeting element. Terminating components having no functional element may be exchanged with terminating components having a functional element by treating the supramolecular structure with a second terminating component or by treating the supramolecular structure with a mixture of other terminating components. Likewise, the supramolecular structure may be prepared using a mixture of terminating components, each of which will be incorporated into the supramolecular structure.

Cargo

In some embodiments of the present invention, the supramolecular structure can include cargo. Cargo is defined as a chemical moiety which can be encapsulated within the supramolecular structure and which can be released from the supramolecular structure. In some embodiments of the present invention, the cargo materials may bind to one or more of the structural components, binding component or terminating component. For some preferred embodiments of the present invention, the cargo is a chemical moiety which does not significantly bind specifically to the binding regions of the binding component and that has the effect that the cargo does not interfere with self-assembly of the nanoparticle. For example, in some embodiments of the present invention, the cargo is a small molecule selected from the group consisting of a therapeutic compound, doxorubicin, taxol, rapamycin, cis-platin, a cancer drug, a cancer therapy chemical, a protein, a peptide, an oligonucleotide, an siRNA, a plasmid, a gene delivery molecule, and any combination thereof.

It is contemplated for some embodiments of the present invention that nanoparticles may not encapsulate the same cargo. In some embodiments of the present invention, the supramolecular structures may deliver therapeutic proteins and oligonucleotides to a target cell, for protecting therapeutic compounds, proteins and/or oligonucleotides from degradation prior to delivery or other uses of the supramolecular structures. In some embodiments of the present invention, the supramolecular structure may include two or more cargo compounds. When a selected ratio of amounts of two or more therapeutic compounds are incorporated in an amount of the supramolecular structures, then this provides a means for providing a selected ratio of therapeutic compounds to a cell. In some invention embodiments, a plasmid and small molecule may be incorporated as cargo. Many kinds of cargoes and the ratios of the different cargos encapsulated by the supra-molecular structure embodiments of the present invention are envisioned.

Methods for Preparing a Supramolecular Structure

The invention includes methods for preparing the supramolecular structures described above by preparing a suspension of structural components and binding components; and adding terminating components to said suspension. The ratio of structural components to binding components to terminating components are selected in accordance with a predetermined size of said supramolecular structures. The structural, binding and terminating components self-assemble into supramolecular structures having a substantially predetermined size. In some cases, the predetermined size is at least about 10 nm and less than about 800 nm (nanometers).

The present invention embodiments include methods for preparing the supramolecular structure embodiments.

One general example method for preparing a supramolecular structure comprises the steps of: preparing a suspension of structural component(s) and binding component(s);
adding terminating component(s) to the suspension of the structural component(s) and the binding component(s) to form a mixture; and
forming the supramolecular structure from the mixture of the terminating component(s) with the structural component(s), and the binding component(s).

Optionally, the general method of preparing the supramolecular structure embodiments further comprises the steps of:
selecting a ratio for the amounts of the structural component(s) to the amount of the binding component(s); and
selecting a ratio for the amounts of the structural component(s) to the amount of the terminating component(s).

Optionally, the general method of preparing the supramolecular structure embodiments further comprises the step of:
selecting a ratio for the amounts of the structural component(s) to the amount of the binding component(s).

Optionally, the general method of preparing the supramolecular structure embodiments further comprises the step of:
selecting a ratio for the amounts of the structural component(s) to the amount of the terminating component(s).

Optionally, the general method of preparing the supramolecular structure embodiments further comprises the step of:
selecting a ratio for the amounts of the binding component(s) to the amount of the terminating component(s).

The ratio of structural components to binding components to terminating components are selected in accordance with a predetermined size of said supramolecular structures. The structural, binding and terminating components self-assemble into supramolecular structures having a substantially predetermined size. In some embodiments of the present invention, the predetermined size is between about 5 nm to 2000 nm. Preferably in some embodiments of the present invention, the predetermined size is at least about 20 nm and less than about 400 nm (nanometers). The size of the supramolecular structures may be easily adjusted by varying the ratios between the components used to prepare the supramolecular structures. A wide variety of supramolecular structures of different sizes may be easily prepared. This also enables combinatorial synthesis, as arrays of supramolecular structures may be assayed based on their specific function to optimize their activity.

The supramolecular structures may be readily prepared by combining the components together. At least three components self-assemble into the supramolecular structure. Additional components (structural, binding or terminating) or cargo compounds may also be used, so long as the minimum elements are present. The additional components may include one or more functional elements.

After the supramolecular structure is formed, components may be exchanged with other components bearing appropriate binding elements or binding regions by treating the supramolecular structure with additional components. For example, terminating components may be exchanged by treating the supramolecular structure with other terminating components (for example, bearing a functional element). Likewise, structural or binding components may be exchanged by treating the supramolecular structure with additional structural or binding components. A suspension or solution of the components may be sonicated to accelerate or assist in component exchange reactions.

The size of the supramolecular structures may be easily adjusted by varying the ratios between the components used to prepare the supramolecular structures. A wide variety of supramolecular structures of different sizes may be easily prepared. This also enables combinatorial synthesis, as arrays of supramolecular structures may be assayed based on their specific function to optimize their activity.

Using component exchange, the size of the supramolecular structures may be adjusted after the supramolecular structures are formed by treating the pre-formed supramolecular structures with additional component. For example, if the pre-formed supramolecular structure is treated with additional binding component, the size will decrease. If the pre-formed supramolecular structure is treated with additional structural component, the size will increase. Examples of this effect are presented in the Examples below.

The supramolecular structures can be disassociated in vitro and in vivo environments according to some embodiments of the current invention.

Functional elements may also be easily adjusted using this method. In many cases, components bearing a functional element may be included in the mixture used to prepare the supramolecular structure. The extent to which the functional elements are present in the supramolecular structure may be readily adjusted by changing the ratio between components having a functional element and components without. For example, if the functional element is present on the binding component, the ratio of the binding component having the functional element and the binding component lacking the functional element determines the extent to which the functional element is present in the supramolecular structure formed. The same holds true when the functional element is present on the terminating component or structural component.

When functional elements are present on terminating components, previously assembled supramolecular structures may be treated with terminating component(s) having a functional element. A portion of the terminating components will exchange to produce a supramolecular structure bearing the functional element(s). Multiple terminating components bearing multiple different functional elements may be added in a similar manner. The extent to which the functional element is present on the resulting supramolecular structure is determined by the concentration of the terminating component used to treat the pre-formed supramolecular structure.

Individual components may be readily prepared using known chemical synthesis methods. The binding elements are selected based on the type(s) of intermolecular forces selected for binding the components together. Based on their molecular recognition chemistry, chemical moieties may be selected as binding elements or binding regions. For structural components, inorganic cores may be synthesized using methods known in the art to provide binding elements on the surface, when needed. Organic compounds, such as polymers and dendrimers, may be synthesized by known methods with suitable binding elements. Alternatively, organic cores, including polymers, dendrimers, and/or polypeptides may be prepared which have reactive functional groups that may be derivatized with suitable binding elements or binding regions.

Numerous methods exist for derivatizing organic compounds with suitable binding elements. For example, reactive functional groups on organic compounds, such as hydroxyls, thiols, amines, carboxylic acids, halides, alkenes, alkynes, azides, and others may be reacted or activated to react with a variety of other functional groups to form covalent bonds. For example, amine-bearing compounds having a free $NH_2$ group may be reacted with binding elements bearing amine-reactive groups such as isocyanates, isothiocyanates, and activated esters, such as N-hydroxy succinimide (NHS) esters. In this way, binding elements may be readily added to any component. The number of binding elements on a particular component may be varied based on the number of reactive sites, and the amount of the reactive binding element used to prepare the component. For specific examples, see the Examples described below.

Chemistry commonly used to derivatize proteins may also be used to add binding elements to proteins, peptides, or antibodies. For example, amine-coupling or thiol-ene coupling can be used to generate irreversible bonds.

In some cases, a linker may be required. Various bifunctional crosslinkers are known to those in the art for covalently bonding to proteins, any of which may be used. For example, heterodifunctional crosslinkers such as succinimidyl-4-[N-maleimidomethyl] cyclohexane-1-carboxylate (SMCC) and melaimidobutyryloxysuccinimide ester (GMBS) may be used to react with amines (via the succinimide esters), and then form a covalent bond with a free thiol (via the maleimide). Other crosslinkers, such as succinimidyl 3-(2-pyridyldithio)-propionate (SPDP) may react with amines (via the succinimide ester) and form a covalent bond with a free thiol via thiol exchange. Other difunctional crosslinkers include suberic acid bis (N-hydro succinimide ester), which can react with two amines. Other bifunctional and heterobifunctional crosslinkers useable with various surface modifications will be evident to those of skill in the art.

In some embodiments of the invention, it is desirable to include a reversible (cleavable) cross-linker, a variety of which will be evident to a skilled worker. For example, 4-allyloxy-4-oxo-butanoic acid has an alkene group on one end that can be used for thiol-ene coupling to thiol, and its other end is a carboxylic group that can be coupled to an amine. There is an ester group in the middle of the cross-linker that should hydrolyze slowly over time under physiological conditions. Other cleavable cross-linkers will be evident to a skilled worker. These include, e.g., disulfide bonds which will cleave upon reduction.

Uses of Supramolecular Structures

The supramolecular structures have a variety of uses, particularly in biological applications. The simple methods required to produce the supramolecular structures enable rapid preparation of supramolecular structures of various sizes or bearing specific functional elements. The use of different materials for structural, binding, and terminating components enables a wide variety of utilities.

The supramolecular structures can be disassociated in vitro and in vivo environments according to some embodiments of the current invention. This enables release of cargo materials from the supramolecular structure.

The supramolecular structures may be used for gene therapy (in vivo) or for cellular transfection (in vitro) by delivering genes or plasmids to cells.

The invention includes methods of delivering a gene to a cell by contacting the cell with a supramolecular structure described herein, bearing a plasmid cargo. Treating the cell with the supramolecular structure results in internalization of the supramolecular structure, followed by release of the plasmid into the cell. This can result in effective "transfection" of the targeted cell with the plasmid of interest. In general, any plasmid, bearing any gene may be introduced into the cell in this manner. Likewise, targeting and/or cell permeation elements may improve cell specificity and/or internalization.

The invention also includes methods of delivering therapeutic compounds by treating a cell with a supramolecular structure described herein, having a therapeutic compound as cargo. The therapeutic compound may be, for example, a protein or peptide (including antibodies), an oligonucleotide (e.g., siRNA) or a small molecule. The small molecule may be, for example, an anti-cancer (e.g. doxorubicin, taxol, paclitaxel, cis-platin, or rapamycin), antibiotic, anti-bacterial, or anti-fungal agent. Functional elements on the supramolecular structure may improve cell targeting, internalization, or distribution. More than one therapeutic compound may be delivered in a single supramolecular structure, and if desired, the ratio of therapeutic compounds may be controlled.

Other methods of using the supramolecular structures described herein include methods of photo-thermotherapy by treating cells with supramolecular structures described herein having gold nanoparticles as structural components.

Pharmaceutical Compositions

The supramolecular structures or nanoparticles discussed herein can be formulated into various compositions, for use in diagnostic or therapeutic treatment methods, especially for viral infection treatment. The compositions (e.g. pharmaceutical compositions) can be assembled as a kit. Generally, a pharmaceutical composition of the invention comprises an effective amount (e.g., a pharmaceutically effective amount) of a composition of the invention.

A composition of the invention can be formulated as a pharmaceutical composition, which comprises a composition of the invention and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, Remington's Pharmaceutical Sciences, 18th ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, or the like.

A pharmaceutical composition or kit of the invention can contain other pharmaceuticals, in addition to the compositions of the invention. The other agent(s) can be administered at any suitable time during the treatment of the patient, either concurrently or sequentially. One skilled in the art will appreciate that the particular formulation will depend, in part, upon the particular agent that is employed, and the chosen route of administration. Accordingly, there is a wide variety of suitable formulations of compositions of the present invention.

Formulations which are suitable for topical administration directly in the CNS include, e.g., suitable liquid carriers, or creams, emulsions, suspensions, solutions, gels, creams, pastes, foams, lubricants, or sprays. Topical administration in the CNS is possible when the CNS is opened by wound or during a surgery. One skilled in the art will appreciate that a suitable or appropriate formulation can be selected, adapted or developed based upon the particular application at hand. Dosages for compositions of the invention can be in unit dosage form. The term "unit dosage form" as used herein refers to physically discrete units suitable as unitary dosages for animal (e.g. human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient. The dose of a composition of the invention, administered to an animal, particularly a human, in the context of the present invention should be sufficient to affect at least a detectable amount of a diagnostic or therapeutic response in the individual over a reasonable time frame. The dose used to achieve a desired effect will be determined by a variety of factors, including the potency of the particular agent being administered, the pharmacodynamics associated with the agent in the host, the severity of the disease state of infected individuals, other medications being administered to the subject, etc. The size of the dose also will be determined by the existence of any adverse side effects that may accompany the particular agent, or composition thereof, employed. It is generally desirable, whenever possible, to keep adverse side effects to a minimum. The dose of the biologically active material will vary; suitable amounts for each particular agent will be evident to a skilled worker.

Another embodiment of the invention is a kit useful for any of the methods disclosed herein, either in vitro or in vivo. Such a kit can comprise one or more of the compositions of the invention. Optionally, the kits comprise instructions for performing the method. Optional elements of a kit include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form.

From the foregoing description, it will be apparent that variations and modifications may be made to the invention described herein to adopt it to various usages and conditions. Such embodiments are also within the scope of the following claims. The recitation of a listing of elements in any definition of a variable herein includes definitions of that variable as any single element or combination (or sub combination) of listed elements. The recitation of an embodiment herein includes that embodiment as any single embodiment or in combination with any other embodiments or portions thereof. Terms listed in single tense also include multiple unless the context indicates otherwise. The examples disclosed below are provided to illustrate the invention but not to limit its scope. Other variants of the invention will be readily apparent to one of ordinary skill in the art and are encompassed by the appended claims. All publications, databases, and patents cited are hereby incorporated by reference for all purposes.

Methods for preparing, characterizing and using the compounds of this invention are illustrated in the following Examples. Starting materials are made according to procedures known in the art or as illustrated herein. The following examples are provided so that the invention might be more fully understood. These examples are illustrative only and should not be construed as limiting the invention in any way.

Various methods of introducing supramolecular combinatorial derivatives of cobalamin (CDC) can be used. The CDC composition can be given orally or can be administered by intravascular, subcutaneous, intraperitoneal injection, in the form of an aerosol, by ocular route of administration, into the bladder, topically, and so on. For example, inhalation methods are well known in the art. The dose of the therapeutic composition will vary widely depending on the particular antiviral CDC administered, the nature of the disease, frequency of administration, route of administration, clearance of the agent used from the host, and the like. The initial dose may be higher with subsequent lower maintenance doses. The dose can be administered with a frequency of once a week or once every two weeks, or divided into smaller doses and administered once or several times a day, twice a week, and so on to maintain an effective dose level. In many cases, a higher dose will be needed for oral administration than for intravenous administration.

The compounds of this invention may be included in a variety of compositions for therapeutic administration. More specifically, the compounds of the present invention can be incorporated into pharmaceutical compositions in combination with suitable pharmaceutically acceptable carriers or diluents and can be incorporated into preparations in solid, semi-solid, liquid or gaseous forms, such as capsules, powders, granules, ointments, creams, foams, solutions, suppositories, injections, forms for inhalation use, gels, microspheres, lotions and aerosols. As such, the administration of the compounds can be carried out in various ways, including oral, buccal, rectal, parenteral, intraperitoneal, intradermal, transdermal, intratracheal administration and so on. The anti-viral CCMs of the invention can be distributed systemically after administration or can be localized using an implant or other composition that holds the active dose at the site of implantation.

The compounds of the present invention can be administered alone, in combination with each other, or they can be used in combination with other known compounds (e.g., perforin, anti-inflammatory agents, and so on). In pharmaceutical dosage forms, the compounds may be administered in the form of their pharmaceutically acceptable salts. The following methods and excipients are given by way of example only and are not in any way limiting. For preparations for oral administration, the compounds can be used alone or in combination with suitable additives for the manufacture of tablets, powders, granules or capsules, for example, with conventional additives such as lactose, mannitol, corn starch or potato starch; with binding agents, such as crystalline cellulose, cellulose derivatives, gum arabic, corn starch or gelatins; with disintegrates such as corn starch, potato starch or sodium carboxymethyl cellulose; with talc or magnesium stearate, and, if desired, with diluents, buffering agents, moistening agents, preservatives and flavoring agents.

The compounds may be included in injectable compositions by dissolving, suspending or emulsifying them in an aqueous or non-aqueous solvent such as vegetable or other similar oils, synthetic aliphatic acid glycerides, esters of higher aliphatic acids or propylene glycol; and, if desired, with conventional additives, such as solubilizers, isotonic agents, suspending agents, emulsifiers, stabilizers and preservatives. The compounds can be used in an aerosol composition for inhalation administration, including with the use of nebulizers. The compounds of the present invention can be incorporated into suitable pressure propellants such as dichlorodifluoromethane, propane, nitrogen and the like. In addition, the compounds can be incorporated into suppositories by mixing with a variety of bases, such as emulsifying bases or water-soluble bases. The compounds of the present invention can be administered rectally using a suppository. A suppository may contain excipients, such as cocoa butter, carbowax, and polyethylene glycols, which melt at body temperature but are solid at room temperature.

Standard dosage forms for oral or rectal administration, such as syrups, elixirs and suspensions, where each unit dose, for example, a teaspoon, tablespoon, tablet or suppository, may contain a predetermined amount of a composition containing one or more compounds of the present invention. Similarly, unit dosage forms for injection or intravenous administration may contain the compound of the present invention in a composition in the form of a solution in sterile water, normal saline, or another pharmaceutically acceptable carrier. Implants for sustained release of compositions are well known in the art. Implants are made in the form of microspheres, plates, and so on with biodegradable or non-biodegradable polymers. For example, lactic and/or glycolic acid polymers form a degrading polymer that is well tolerated by the host.

The implant containing the antiviral combinatorial cobalamides according to the invention is positioned close to the site of infection (in case of respiratory viral infection, the lungs and bronchi), so that the local concentration of the active agent is increased compared to other areas of the body. The term "unit dosage form" refers to physically discrete units suitable for use as single doses for human and animal subjects, each unit containing a predetermined number of compounds of the present invention, which, according to calculations, is sufficient to provide the desired effect together with a pharmaceutically acceptable diluent, carrier or excipient. The descriptions of the unit dosage forms of the present invention depend on the particular compound used, and the effect to be achieved, and the pharmacodynamics of the compound used in the host. Pharmaceutically acceptable excipients, such as excipients, adjuvants, carriers or diluents, are generally available.

In addition, pharmaceutically acceptable excipients are generally available, such as pH adjusting agents and buffering agents, tonicity agents, stabilizers, wetting agents and the like. Typical doses for systemic administration range from 0.1 pg (picogram) to 1000 milligrams per kg of subject body weight per administration. A typical dose may be a single tablet for administration from two to six times a day, or one capsule or sustained release tablet for administration once a day with a proportionally higher content of the active ingredient. The effect of prolonged release may be due to the materials of which the capsule is made, dissolving at different pH values, capsules providing a slow release under the influence of osmotic pressure or by any other known controlled release method. It will be clear to those skilled in the art that dose levels may vary depending on the particular compound, the severity of the symptoms, and the subject's predisposition to side effects. Some of the specific compounds are more potent than others.

Preferred doses of this compound can be readily determined by those skilled in the art in a variety of ways. A preferred method is to measure the physiological activity of the compound. One of the methods of interest is the use of liposomes as a vehicle for delivery. Liposomes fuse with the cells of the target region and ensure the delivery of liposome contents into the cells. The contact of the liposomes with the cells is maintained for a time sufficient for fusion using various methods of maintaining contact, such as isolation, binding agents and the like. In one aspect of the invention, liposomes are designed to produce an aerosol for pulmonary administration. Liposomes can be made with purified proteins or peptides that mediate membrane fusion, such as Sendai virus or influenza virus.

Lipids can be any useful combination of known liposome forming lipids, including cationic or zwitterionic lipids, such as phosphatidylcholine. The remaining lipids will usually be neutral or acidic lipids, such as cholesterol, phosphatidylserine, phosphatidylglycerol and the like. To obtain liposomes, the method described by Kato et al. (1991) J. Biol. Chem. 266: 3361. Briefly, lipids and a composition for incorporation into liposomes containing combinatorial supramolecular cobalamides are mixed in a suitable aqueous medium, suitably in a salt medium, where the total solids content will be in the range of about 110 wt. %. After vigorous stirring for short periods of approximately 5-60 seconds, the tube is placed in a warm water bath at approximately 25-40° C. and this cycle is repeated approximately 5-10 times. The composition is then sonicated for a suitable period of time, typically approximately 1-10 seconds, and optionally further mixed with a vortex mixer. Then the volume is increased by adding an aqueous medium, usually increasing the volume by about 1-2 times, followed by agitation and cooling. The method allows to include supramolecular structures with high total molecular weight in liposomes.

Compositions with Other Active Agents

For use in the methods under consideration, a number of anti-viral supramolecular structures have been contemplated. One anti-viral supramolecular structure is called KS. Anti-viral KS of the invention may be included in compositions with other pharmaceutically active agents, in particular other antiviral, antimicrobial or anti-cancer agents. Other agents of interest include a wide range of anti-viral derivatives of mononucleotides and other RNA polymerase inhibitors known in the art. Classes of antiviral agents include interferons, lamivudine, ribavirin, and so on; amantadine; remantadine, such as zinamivir, oseltamivir, and so on; acyclovir, valaciclovir, valganciclovir, and so on. Other groups of antiviral agents include adefovir, vbacavir, didanosine, emtricitabine, lamivudine, nelfinavir, ritonavir, sakinavir, daclatasvir, stavudine, tenofovir, efavirenz, nevirapine, indinavir, lopinavir and ritonavir, nelfinavir, ritonavir, sofosbuvir, methylcarbylamine, hydroxocobalamin, vanillin, cholecalciferol. Cytokines, such as interferon gamma, tumor necrosis factor alpha, interleukin 12, and so on, may also be included in the CCM composition of the invention. The present invention is further described by the following examples, which should not be construed as limiting the scope of the invention.

Alkylation is defined as the introduction of an alkyl substituent in an organic molecule. Typical alkylating agents are alkyl halides, alkenes, epoxy compounds, alcohols, less often aldehydes, ketones, esters, sulfides, diazoalkanes. The alkylation catalysts are mineral acids, Lewis acids, and also zeolites. Alkylation is widely used in the chemical and petrochemical industries.

An ensemble or supramolecular ensemble is a term from supramolecular chemistry. For the present invention, the objects of supramolecular chemistry are ensembles built spontaneously from complementary geometrically and chemically corresponding molecular fragments. When synthesizing supramolecular structures from one combinatorial derivative with incomplete substitution of available groups, more than 100 different derivatized supramolecular structures can be synthesized due to the possible chemical permutations and combinations. Notably, intermolecular ionic and hydrogen bonds are necessarily formed between their molecules and the derivatized supramolecular structures have a significantly higher biological activity than the original cyanocobalamin molecule.

Using present invention processes, a drug was made which is effective in vivo against influenza, herpes, in Ovo (in egg) models, and cattle coronavirus. To make the drug, we used a combinatorial mixture of carboxymethyl cobalamin in the form of a supramolecular ensemble without separation into separate components.

A combinatorial library is a set of a large number of chemical compounds, proteins, genes or oligonucleotides allowing you to quickly search for target genes or target proteins. For example, a combinatorial library kit can consist of millions of different chemicals, or for example, a set of recombinant DNA molecules obtained by inserting various antibodies in the light and heavy chains of cDNAs.

Combinatorial synthesis involves synthesis by methods of combinatorial chemistry, of a variety of simultaneous reactions between three or more reagents with the formation of combinatorial synthesis products which comprise of hundreds of derivatives of the combined reagents. The derivatives of the combined reagents can be separated chromatographically so as to confirm their structure and to study the biological activity. Recent approaches include using non-separated or/and non-purified mixtures of combinatorial synthesis products for various reasons which include that such mixtures of combinatorial synthesis products have more significant and more variable biological activity profiles than the biology profiles of the separated components of the combinatorial synthesis products.

Therapeutically effective amount (TEA) is a term for the present invention which refers to the drug amount. For some embodiments of the present invention a therapeutically effective amount of combinatorial derivatives of cyanocobalamin is an amount which provides a therapeutically effective antiviral activity. The TEA is expected to differ for different viruses, and different animal models.

EXAMPLES

Figure 5:
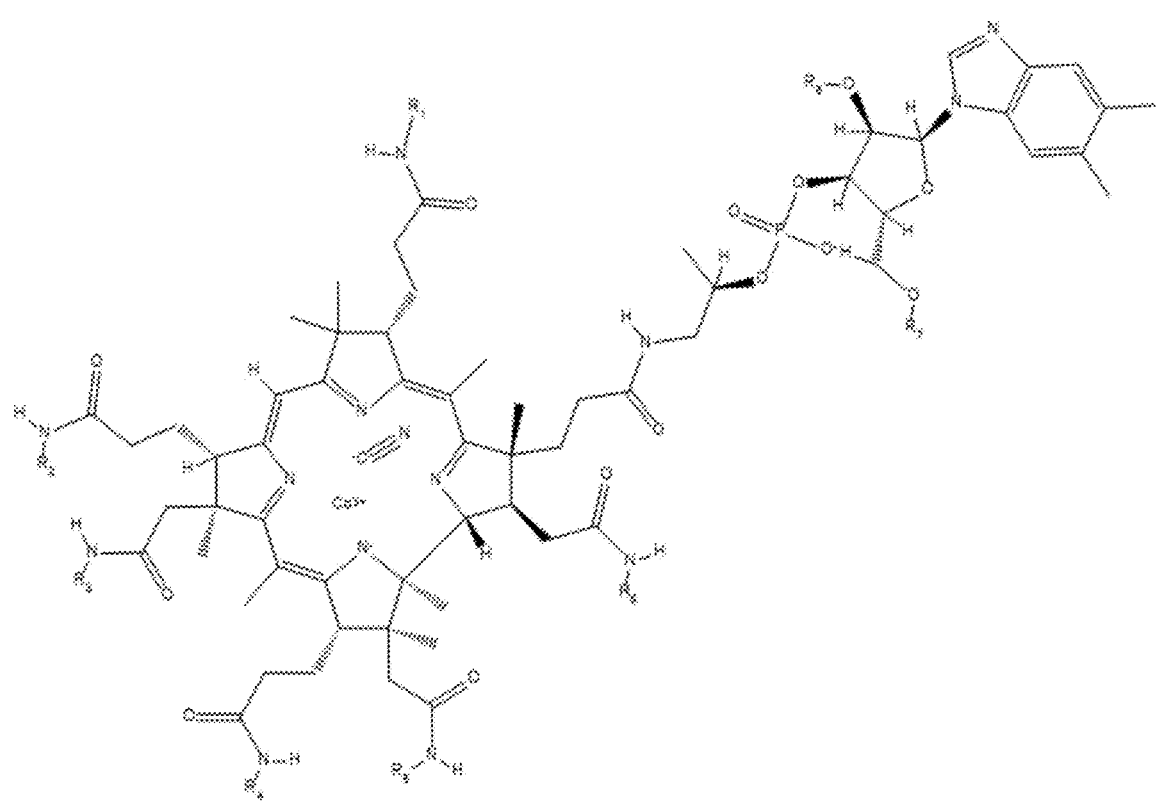
FIG. 5 depicts a structure of dynamic self-assembled combinatorial derivatives of cyanocobalamin.
Figure 6:
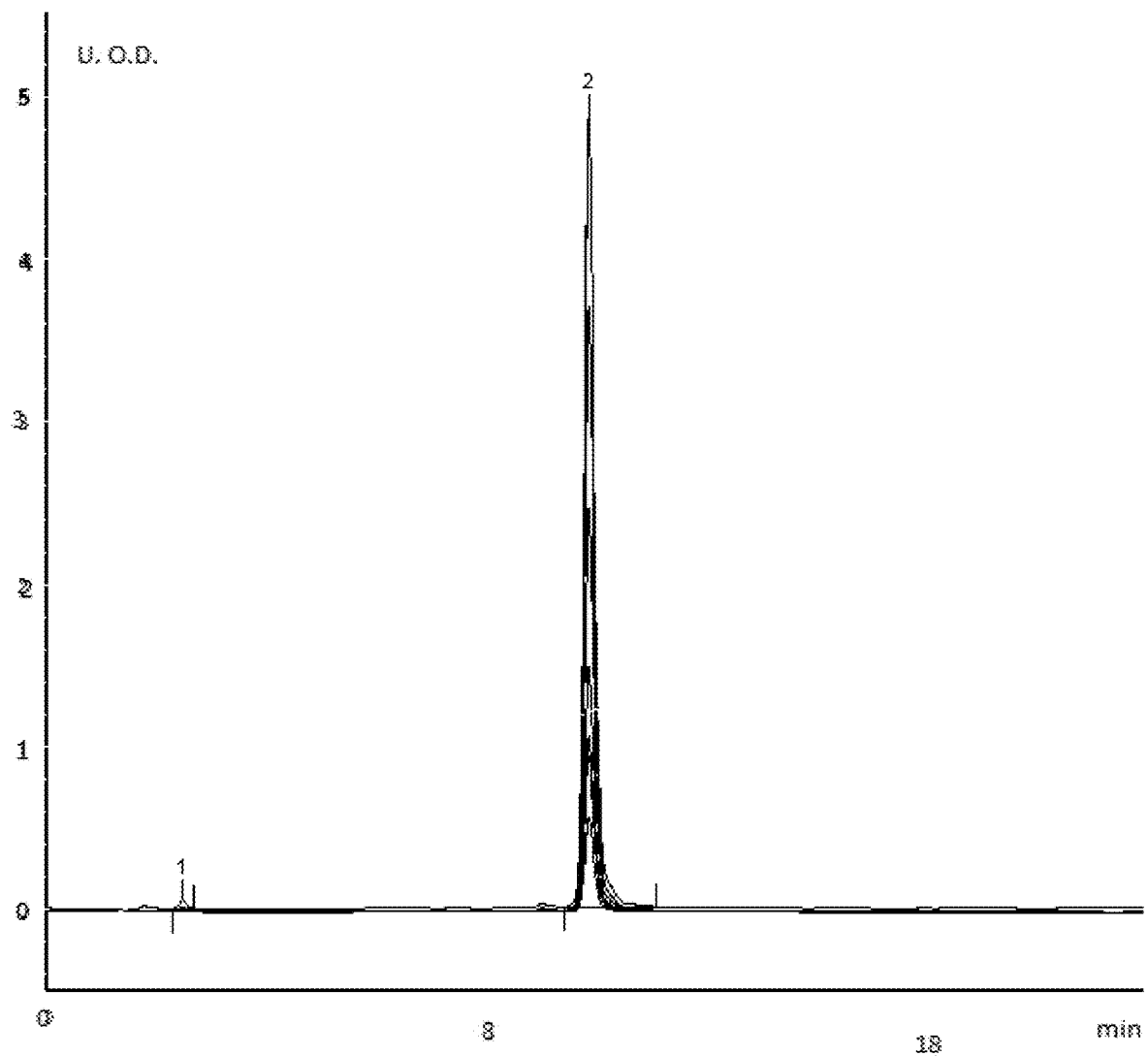
FIG. 6 presents an HPLC record of the initial cyanocobalamin with chromatographic conditions which are a gradient separation using a buffer A which comprises 0.1M perchloric acid with 1M lithium perchlorate, and a buffer B which comprises an acetonitrile gradient (from 5% to 100%) on a Milichrome A-02 chromatograph with a prontosil-18 column.
Figure 7:
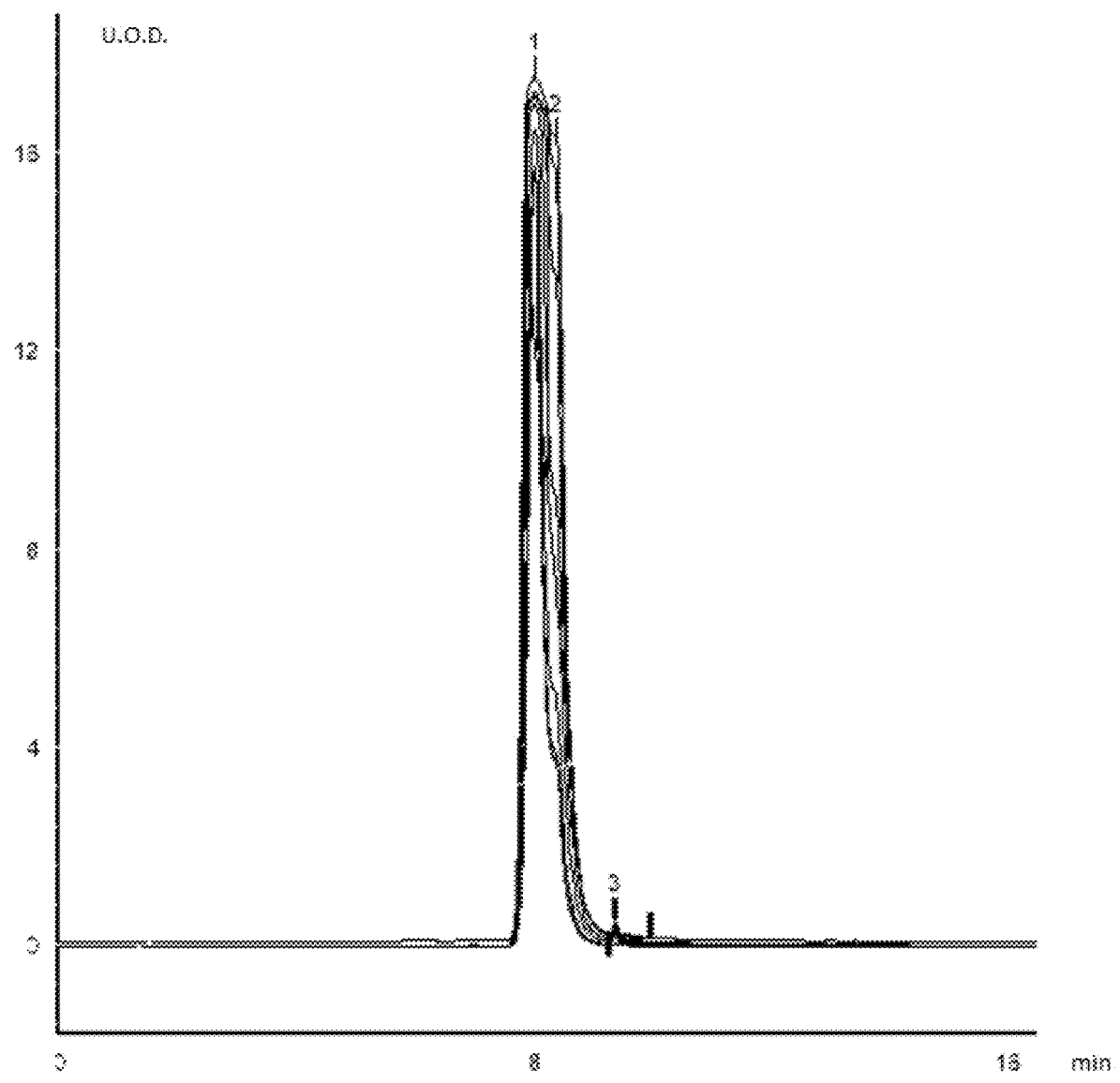
FIG. 7 presents an HPLC record of the combinatorial derivative of cyanocobalamin with 128 derivatives with chromatographic conditions which are a gradient separation using a buffer A which comprises 0.1M perchloric acid with 1M lithium perchlorate and a buffer B which comprises an acetonitrile gradient (from 5% to 100%) on a Milichrome A-02 chromatograph with a column prontosil-18.

EXAMPLE 1 is an example of practicing the present invention using a combinatorial-modified cobalamin serving as the core of a supramolecular structure. This core is synthesized using combinatorial derivatives of cyanocobalamin with antiviral properties and called KS. Then pharmaceutical compositions and dosage forms which are created, are characterized in that the alkylated derivatives of cyanocobalamin are an undivided combinatorial mixture of derivatives from mono-substituted to fully-substituted derivative for all groups $R_1$-$R_7$ of the following structure depicted in FIG. 5 where at least one of the substituents $R_1$-$R_7$ is —$CH_2$—COOM in any position, and M is a metal or hydrogen atom. M can also be represented by one of the metals: K, Mg, Ca, Cu, Fe, Li, Na, Ba, Ag, Pt, Au, Ti, or Sb. In another embodiment of the invention, the pharmaceutical composition may further comprise vanillin in the composition of the dosage form and cholecalciferol. In another embodiment of the invention, the pharmaceutical composition may further comprise an unsubstituted methyl cobalamin, a hydroxocobalamin (hydroxycobalamin), a cobamamide or a mixture thereof in the dosage form. The proposed pharmaceutical compositions, for example, can be formulated into various dosage forms, including, but not limited to an aerosol formulation for use in a nebulizer or spray, of for use an injectable formulation for intramuscular injection (IM), intravenous (IV) injection, and intravenous (IV) infusion.

A virucide is defined as any physical or chemical agent that deactivates or destroys viruses. This differs from an antiviral drug, which inhibits the proliferation of the virus (Virucide, Wikipedia, 2020). As adjectives the difference between viricidal and virucidal. is that viricidal is of or pertaining to a viricide while virucidal is killing viruses. (virucidal vs. viricidal, Wikki-diff, 2020).

EXAMPLE 2 is an example synthesis a combinatorial mixture of carboxymethylated cyanocobalamin which can be used to make an anti-viral supramolecular structure called KC.

The synthesis is as follows: 1 Mmol (millimole) of cyanocobalamin is dissolved in 50 ml of TRIS-buffer solution, and 4 Mmol of monochloroacetic acid is added with stirring until both components are completely dissolved and then the solution is stirred with a thermostat set at 40° C. for 7 days. Then the solution is poured into vials, lyophilized so excess of monochloroacetic acid and hydrochloric acid distill off, and used for analysis and research. The synthesis Example 2 can create $2^7$ derivatives (128 derivatives) of carboxymethylated cyanocobalamins.

FIG. 6 shows a chromatogram HPLC (high pressure liquid chromatography) graph analysis of the original cyanocobalamin. The initial cobalamin gives one absorption line when using a UV-detector.

FIG. 7 shows a chromatogram HPLC graph analysis of a combinatorial derivative of cyanocobalamin. The chromatogram shows that the peak of the derivative is not only located in another place. Derivatives with a more hydrophilic region leave the HPLC column sooner and thus the chromatogram signature of the derivatives is broadened, and divided into additional bands. This suggests that the derivatives of cyanocobalamin can have intramolecular and supramolecular ionic and hydrogen bonding that remain intact during the HPLC separation process performed under classical conditions by gradient HPLC. It was also not possible using thin-layer chromatography (TLC) and capillary gel electrophoresis (CGEP) to separate and identify fragment of the supramolecular structure. Other chemical combinations can be used to derivatize cyanocobalamin include using carboxylic acid anhydrides and polycarboxylic acid anhydrides, carboxylic acid halides, and halocarbons. For some embodiments of the present invention methyl cobalamin, hydroxocobalamin (hydroxycobalamin), or/and cobamamide may be used as the primary cobalamin for derivatization.

Further, in an experiment on the study of anti-viral activity ($ED_{90}$=10-30 μg/ml), several liquid dosage forms were studied. One anti-viral liquid dosage form that was studied is KS (the pure combinatorial derivative). A second anti-viral liquid dosage form that was studied is KC which is a mixture of KS with vanillin (van) and cholecalciferol (C). Thus, in notation form: KC=(KS+van+C). A third anti-viral liquid dosage form that was studied is KSO which is a mixture of KS with vanilla (van) and cobamamide (CO). Thus in notation form: KSO=(KS+van+CO).

To check the biological (antiviral) activity of the synthesized KC derivatives, the antiviral activity of the derivatives was studied by the screening method on models of the H1N1 influenza virus (Inf), the reference strain of vesicular stomatitis virus (Vesic.—VVS) and herpes simplex virus type 1 (Herp.—strain L-2), coronavirus-infectious bird bronchitis virus (IBP) in tablets on chicken fibroblast culture according to the degree of degradation (cytopathic effect, detachment from the bottom of the hole). The degree of "desquamation" of the cells was determined by staining the culture with a vital dye, the concentration of which was determined spectrophotometrically relative to a healthy monolayer and an empty well. The results of in vitro studies are shown in Table 1 below.

TABLE 1

Antiviral activity of supramolecular combinatorial derivatives of cyanocobalamin KS and its dosage forms

| | %, cytoprotective antiviral action ** | | | |
|---|---|---|---|---|
| Composition | Inf | Herp | Vesic | IBP |
| KS | 75 | 80 | 74 | 82 |
| | 70 | 58 | 94 | 80 |
| | 79 | 66 | 90 | 73 |
| | 89 | 89 | 96 | 77 |
| | 100 | 93 | 100 | 79 |
| n ± N, % | 83 ± 12 | 77 ± 15 | 91 ± 10 | 78 ± 3 |
| KS + van | 94 | 100 | 94 | 80 |
| | 93 | 95 | 93 | 89 |
| | 98 | 90 | 98 | 90 |
| | 100 | 100 | 100 | 100 |
| | 100 | 100 | 83 | 100 |
| n ± N, % | 97* ± 3 | 97* ± 4 | 94* ± 7 | 92* ± 8 |
| KS + van + CO | 90 | 88 | 94 | 100 |
| | 100 | 70 | 100 | 100 |
| | 100 | 100 | 94 | 100 |
| | 93 | 100 | 95 | 92 |
| | 80 | 100 | 100 | 88 |
| n ± N, % | 93* ± 8 | 92* ± 13 | 97* ± 3 | 96* ± 6 |
| Negative control of pure culture (without virus) | 100 | 100 | 100 | 100 |
| Positive control of infected culture (with virus without treatment) | 0 | 10 | 5 | 0 |

*groups (KS + van) and (KS + van + CO) are statistically significantly more effective than pure KS.

** for an average effective dose of 10 μg/ml.

As can be seen from Table 1, all variants of dosage forms based on KS have an antiviral effect that can protect 50% or more cells of an infected culture. Dosage forms with vanilla and other derivatives of cobalamin statistically significantly ($P<0.05$) exceed the effectiveness of the pure substance KS. The following types of transplantable cells of human and animal origin were used to determine the maximum tolerated concentration (MTC) in toxicological experiments and study the antiviral activity of the drug KS and its dosage forms for injection: PT, Tr, Ner-2, Hela, and Chicken embryo. PT means transplantable cells of the kidney of the cattle embryo. Tr means tracheal cells of the cattle embryo. Ner-2 means transplantable cells of human larynx cancer. Hela means transplantable cancer cells of the uterus.

Cells were grown in 199 medium supplemented with 10% bovine serum and antibiotics (penicillin and streptomycin). Influenza viruses (H1N1), vesicular stomatitis (Indiana strain), coronavirus (X 343/44) and herpes simplex virus type 1 (strain L-2), coronavirus of infectious bronchitis of birds (strain IEK-KL2) were used as test viruses. The studies were carried out according to the methods recommended by the State Pharmacological Center of the Ministry of Health of Ukraine.

Toxicity Study—MTC Determination for KS And KS Dosage Forms on Cell Cultures and Chicken Embryos Two-day cell cultures with a well-formed cell monolayer were used to determine MTC. KS and its KS dosage forms were tested on four cells types above listed (n=5 experiments). In each experiment, at least 10 test tubes of each culture were used. After removal of the growth medium from the tubes, 0.2 ml of the test solution and 0.8 ml of the supporting nutrient medium were added. Tubes with cells were incubated at 37° C. for 7-8 days. Control experiments were tubes with cell cultures with no drug added.

The presence or absence of a cytopathic effect was included a part of the experiment's test results. The presence or absence of a cytopathic effect (CPE) was determined by viewing the cells under a microscope at 10× magnification. The degree of cytotoxic action was assessed by using a four-plus system (+, ++, +++, ++++) to grade the change in the morphology of the cells: (1) rounding and wrinkling of cells, and (2) rejection of degenerated cells from the glass.

The maximum tolerated concentration (MTC) was determined by determining the maximum amount of a substance that did not cause a cytopathic effect on the cells. For this determination, various dilutions of the drug in a 0.2 ml volume dose were added to a cell culture.

To study the in vivo toxicity of the drug at various doses of the drug, dose of the drug in a volume of 0.2 ml were used on 10-11 day old chicken embryos (5 embryos per MP dilution). The drug dose was introduced into the allantois cavity of the chicken embryo using the following procedure. A 10-11-day-old embryos was ovo-scoped, and labeled by a pencil mark on the air bag on the side opposite to the location of the embryo, where there are fewer blood vessels. The pencil marked location was disinfected with an alcoholic iodine solution, and then the shell was punctured, and then 0.2 ml of the drug dose was injected into the hole with a tuberculin syringe into the allantois cavity with the syringe needle at a depth of 10-15 mm parallel to the longitudinal axis of the egg. After the injection was made, the shell hole was again disinfected with an alcoholic iodine solution and sealed with paraffin wax. The egg was then placed for incubation using a thermostat set to a temperature of 35-37° C. for 72 hours. Before then opening eggs, they were placed for 18-20 hours in a refrigerator at a temperature of 40° C. to maximize the narrowing of embryo's blood vessels. After this, the eggs were placed on a tray with its blunt end up. Then the shell above the air bag was disinfected with an alcoholic iodine solution and 96% ethanol. The egg was broken and the embryo was removed with sterile tweezers. The membrane lining the bottom of the air sac was also removed, having previously separated it from the underlying chorion-allantois membrane. The number of living and normally developing embryos after 24 and 48 hours of incubation in a thermostat at 37° C., was counted to calculate $LD_{50}$ and MTD according to the Kerber method.

As a result of these experimental studies, KS and its dosage forms were found to be non-toxic to cell cultures at a KS dose of more than 50 mg/ml. Note that to increase the concentration of the drug, the drug solution was lyophilized and then diluted to become a 5% drug concentration.

The results of the study of toxicity of KS in different cultures are presented in Table 2 below.

TABLE 2

The toxicity of KS and its dosage forms on cell cultures

| No п/п | a) Cells culture | Toxicity (mg/ml) |
|---|---|---|
| | KS substance | |
| 1 | PT | More than 50 |
| 2 | Tr | -//- |
| 3 | Hep -2 | -//- |
| 4 | Hela | -//- |
| | K S + van | |
| 5 | PT | More than 50 |
| 6 | Tr | -//- |
| 7 | Hep -2 | -//- |
| 8 | Hela | -//- |
| | K S + van + CO | |
| 9 | PT | More than 50 |
| 10 | Tr | -//- |

TABLE 2-continued

The toxicity of KS and its dosage forms on cell cultures

| No п/п | a) Cells culture | Toxicity (mg/ml) |
|---|---|---|
| 11 | Hep -2 | -//- |
| 12 | Hela | -//- |

The MTC for cell cultures treated with both pure KS and its dosage forms is more than 50 mg/ml, which indicates the low toxicity of the proposed tool. For further research, we have selected the most effective sample of the dosage form KS + van + CO, then KSO Study of Anti-viral Effect of Drug KSO on Influenza A Virus (H1N1)

For further research, a preferred embodiment of the present invention was selected. This is KSO which is a liquid anti-viral formulation of (KS+van+CO). Aqueous solutions of KSO in various doses (ten-fold dilutions) were administered to 15 chicken embryos in the allantois cavity in a volume of 0.2 ml 12 hours after the virus was introduced in a working dose (100 $TCD_{50}$/0.2 ml). Each experiment was accompanied by control of the test virus in the working dose. Infected and non-infected (control) embryos were incubated at 36° C. for 48 hours. Then, the embryos were opened, from which the allantois fluid was aspirated. Titration of the virus in allantois fluid was carried out according to the generally accepted method with 1% red blood cells of 0 (1) human blood group. Defined coefficient of protection (PC).

The virus titer in the experimental and control groups of chicken embryos is presented in Table 3 below.

TABLE 3

Effective CSO concentration in the in Ovo influenza infection model

| Group | The concentration of the drug (mg/ml) | Viruses titer (lg $TCA_{50/Mn}$) experiment | control | Minimum effective concentration (IEC mg/ml) |
|---|---|---|---|---|
| Control (0.9% sodium chloride solution was injected) | — | 12 | 12 | — |
| Experienced | 50 ± 5 | 0 | 12 | 0.005 |
| | 5 ± 1 | 0 | 12 | |
| | 0.5 ± 0.05 | 1 | 12 | |
| | 0.05 ± 0.005 | 2 | 12 | |
| | 0.005 ± 0.0005 | 5 | 12 | |
| | 0.0005 ± 0.00005 | 10 | 12 | |

As can be seen from Table 3, the minimum effective concentration (IEC) in relation to the influenza virus, which inhibits the synthesis of the virus in 50% of the cells, is equal to 0.005 mg/ml with increasing dilution of the drug, the effectiveness of KSO decreases and has a dose-dependent nature. This fact indicates the presence of a direct antiviral effect in KSO in relation to the H1N1 influenza virus. The term: lg for the present invention means a base 10 logarithm or a decimal logarithm as opposed to a natural logarithm.

Study of Anti-viral effect of Drug KSO on Cytopathic Viruses (Vesicular Stomatitis Virus, Coronavirus, Measles Virus)

Antiviral activity against the cytopathic viruses: Vesicular stomatitis virus, Coronavirus, and Measles virus was determined in a culture of the above cells. The reaction was carried out in the following way: 0.2 ml of the corresponding virus in a working dose (100 $TCA_{50}$/0.2 ml) was added in a volume of 0.2 ml in a 2-day washed cell culture. Then 0.8 ml of support medium was added. When the CPE (cytopathic effect) appeared in the culture, KSO was introduced in various doses. As a control, the same was done with test viruses without the drug. Cells were incubated at 37° C. in an incubator. Experiment data and observations were made on days 3, 5, and 7 of the experiment. The decrease in virus titer under the influence of the test drug by 2 lg units or more in comparison with the control was evaluated as a manifestation of antiviral activity.

The results of study of antiviral activity of the drug KSO are presented in Table 4. Table 4. The study of the antiviral effect of the KSO against viruses: vesicular stomatitis, coronavirus, measles virus)

| Composition | Virus | MEC, МГ/Мл | Maximum drop in virus titer, lg $TCA_{50/mL}$ |
|---|---|---|---|
| K SO | VVS | 0.05 | 4.9 |
| | CV | 0.05 | 3.0 |
| | MV | 0.05 | 4.7 |

As can be seen from Table 4, KSO has antiviral activity and the ability to suppress the reproduction of all the viruses studied by us at a concentration of 0.05 mg/mL ($ED_{90}$) with MPC=50 μg/ml. CTI of the drug is 1000. In addition, KSO was active against all studied viruses. Thus, the drug KSO is not associated with specific characteristics of the virus or cell culture but affects the mechanisms common to all cells.

Study of Anti-Viral Effect of KSO on In Vitro Models of Farm Animal Viruses

Tests were performed in 96-well plastic plates with porcine transmissible gastroenteritis virus (TGS) strain D-52 with an initial titer of 104.0 $TCD_{50}$/ml (tissue cytopathic doses) in a transplanted piglet test cell culture (PTP) and large diarrhea virus cattle strain "Oregon" with an initial titer of $10^7$ $TCD_{50}$/ml in a transplanted culture of saiga kidney cells (PS).

When testing the virus-static (inhibitory) action, cell cultures were infected with viruses at doses of 100 and 10 $TCD_{50}$/ml and incubated in an incubator at 37° C. CSR in various doses was introduced into cell cultures (CC) 1-1.5 hours after infection (after adsorption period). For each dilution took 8 holes. After making the compound, the cell cultures were incubated at 37° C. for 72-144 hours until a clear manifestation of CPE (cytopathogenic effect) in the control of viruses. Virus infected cell cultures, intact CC and CC, where only different concentrations of KSO were introduced, served as controls. Virus-static effect was determined by the difference in titer of viruses in the experiment and control.

When determining the viricidal (inactivating) effect, different doses of the compound solution were mixed in equal volumes with virus-containing material and incubated in an incubator at 37° C. for 24 hours. A virus-containing material was used as a control, to which a placebo (saline) and intact cell cultures were added instead of a compound solution. The mixtures after contact were titrated in parallel with the control. The results were taken into account 72-144 hours after incubation at 37° C., after a clear manifestation of CPE in virus controls. The viricidal effect was determined by the difference in titer of viruses in the experiment and control and expressed in lg TCD50.

From these studies, it was found that the KSO compound at a concentration of 40 μg/ml suppressed the reproduction of the TGS virus by 2.75 lg $TCD_{50}$/ml, at an infectious dose of 100 $TCD_{50}$/ml and in the same dose by 3.75 lg $TCD_{50}$/ml, an infectious dose of 10 $TCD_{50}$/ml. At a dose of 40 μg/ml, KSO inactivated the TGS virus on 2.0 lg $TCD_{50}$/ml. The KSO composition at a dose of 40 μg/ml inactivated cattle diarrhea virus at 4.9 lg $TCD_{50}$/ml.

Thus, the KSO compound has a viral-static (inhibitory) and viricidal (inactivating) effect on TGS viruses and cattle diarrhea, and chemo drugs can be created on its basis for the treatment and prevention of infectious diseases of viral etiology.

Study of KSO Anti-viral Activity in Rabbits with Experimental Herpes Virus Kerato-Conjunctivitis/Encephalitis Herpetic experimental infections are important to study because herpetic diseases are widespread and extremely variable in their clinical manifestations. Models of experimental herpes in animals are finding wider application in the study of new antiviral substances. One clinical forms of systemic herpes which is herpetic encephalitis, is readily produced in guinea pigs, hamsters, rats, mice, rabbits, dogs, and monkeys.

Herpetic keratoconjunctivitis in rabbits (average weight of 3.5 kg) was produced by applying infectious material (herpes simplex virus type 1 strain L-2) on a scarified cornea after eye was anesthetized with dikain instillation and the cornea was scratched several times with a needle. Then the eyelid was closed and rubbed in circular motions. Virus dose was 0.05 ml dose of 6.75 lg $TCD_{50}$/ml. In this series of experiments, 16 rabbits were used. Ten rabbits were injected with KSO (daily from the second day of infection to 14 days) at a dose of 20 mg/kg, and six rabbits were placebo injected with 0.9% sodium chloride solution.

After infection of the rabbit's cornea by HSV1, presence of kerato-conjunctivitis, encephalic disorders and HSV1 antigens in the peripheral blood lymphocytes by the RIF Method were monitored daily. Prior to infection, lymphocytes in all animals lacked specific luminescence, which indicated the absence of type 1 herpes virus antigens in the peripheral blood. On day 3 after infection in all animals, the HSV1 antigen was determined in the blood, IF=70%. Three rabbits (two from the experimental group before treatment and one from the control group) developed encephala manifestations—convulsive syndrome, and lack of appetite. All animals developed kerato-conjunctivitis. On the 4th day after infection, the experimental group of rabbits was injected with KSO in the ear vein at a dose of 20 mg/kg body weight, with 0.9% sodium chloride solution was injected in control group ear vein. Every day for two weeks, this procedure was repeated, once a day. All experimental group animals survived, and HSV1 antigen in the blood was not found on days 13-14 and encephala manifestations ended on 7th day of drug administration, while 2 control group animals died. On 14th day, one experimental group animal had died whereas 6 animals died in KSO-untreated control group. The efficacy index of KSO was 83.3% in the rabbit model of herpetic kerato-conjunctivitis/encephalitis and the experimental rabbit group gained weight. The chemotherapeutic index for was 1000. KSO is an effective antiviral drug with a wide spectrum of action and low toxicity.

Anti-Viral Effect of the Drug KSO on Chicken Broilers Cross Cobb-500

The KSO drug effect on reproduction of vaccine virus strains was measured based on KSO effect to reduce titer of the corresponding specific antibodies. Many antiviral drugs suppress reproduction of live vaccine strains of viruses while inhibiting synthesis of specific antiviral antibodies. This effect is associated with insufficient infectious process intensification by the vaccine and a weak immune response. For example, birds with an infectious bursal disease that are exposed to a live vaccine can make excessive antibodies, so the bird becomes overly-sensitive to other viruses, losses weight and there is increased mortality. The use of the KSO drug was supposed to show the presence of antiviral properties in several ways: reduction of the excess level (titers) of antibodies, decrease in the case (safety), increase in weight gain.

In the experiment, Chicken broilers were taken on days 36 and 41 for 15 animals per group. KSO was drunk the day before vaccination with live vaccines against IBD, Gambaro disease (HD) and coronavirus infectious bronchitis (TB). In the control were Chicken Broiler birds that were not fed KSO but were vaccinated.

Table 5 and Table 6 show the research results of these studies.

TABLE 5

The gain of broilers (at the time of slaughter) in the experimental and control groups

| Indicator | Weight gain **, + % | Safety **, + % |
|---|---|---|
| Experienced group (n = 15) | 7.6 ± 0.7* | 1.0 ± 0.1* |
| Control group (n = 15) | −1.8 ± 0.6* | −4.6 ± 0.4* |

*against unvaccinated control, which was taken as a basis.
** (P < 0.01)

As can be seen from Table 5, in the experimental group, the weight gain of animals increased by (7.6±0.7) % against weight reduction in the control group vaccinated but not treated (−1.8±0.6) %. Also, in the experimental group there was an increase in safety by (1.0±0.1) %. Table 6 shows the changes in the titers of specific antiviral antibodies in the treated KSO vaccinated group, the vaccinated untreated group and the unvaccinated group.

TABLE 6

Change in antibody titer against IBD, BG and IB in vaccinated groups and unvaccinated control

| | The mean change in the titer of specific antibodies ± T | | |
|---|---|---|---|
| | IBB | BG | IB |
| Experimental group (vaccinated and treated with KSO) (n = 15) | −2000 ± 200 | −700 ± 100 | −1000 ± 300 |
| Control group No. 1 (vaccinated but not treated with KSO) (n = 15) | +3000 ± 780 | +3600 ± 1000 | +3000 ± 820 |
| Control group (untreated and not vaccinated) | | 0 | |

As can be seen from Table 6, KSO has a direct (non-immunostimulant) effect against all three viruses. The greatest inhibitory effect was observed in the group with infectious bronchitis—reduction in antibody titer by 2000 units. In the vaccinated, but untreated control, antibody titers increased from 3000 units to 3600 units, indicating an effective process of reproduction of the live vaccine's virus in the bird. Thus, the use of KSO will make it possible to increase the gain of Chicken broilers birds by 5% and to reduce the death rate by 1%. KSO has a direct antiviral effect, inhibiting the reproduction of viruses of infectious bursal disease, Gambaro disease and coronavirus infectious bronchitis.

KSO allows moderate suppression of the replication of vaccine viruses, providing a sufficient level of protective antibodies and preventing the depletion of the immunity of birds and a corresponding decrease in weight gain and an increase in mortality.

KSO Effect on Effectiveness of Chicken Broilers Vaccination by Live Vaccines

The influence of KSO on the vaccination effectiveness was carried out directly in the poultry farm when growing chicken broilers. In the patho-anatomical study of chicken broilers (also simply known as broilers), characteristic changes were observed for colibacteriosis, coccidiosis, as well as numerous hemorrhages on the mucous membranes of the direct intestine, in the area of transition of the glandular stomach to the muscular, basal glands. The contents of the glandular stomach were stained green. The death of broilers reached about 15-20%. In the study of broiler blood serum at 38-42 days of age, specific titers of antibodies to the New Castle disease virus (NCV) were found to be higher than protective ones in the hemagglutination-delayed reaction (HADR) (1:1024, 1:2048).

Study of the effect of KSO at a dose of 0.03 ml/kg live weight on the effectiveness of vaccination against BNK. For this, one of the houses was taken for control, the others were experienced (See Table 7).

TABLE 7

The results of a study the KSO influence on the vaccination effectiveness in poultry

| Group number | Birdhouse number | The number birds (thousand) | Application chart |
|---|---|---|---|
| control | 3 | 40.0 | KSO did not give |
| Experience 1 | 12 | 40.0 | From 7 days age for 3 days before vaccination with live viral vaccines |
| Experience 2 | 6 | 40.0 | 1 day before vaccination against BNK |
| Experience 3 | 9 | 40.0 | Within 3 days before vaccination and 7-10 days after vaccination against BNK |

Inspection conditions, microclimate parameters, light conditions, planting density, feeding conditions were the same in all groups according to the guidelines for growing POC 308 cross.

Immunity was determined at the age of 42 days in HADR. At the same time, the clinical condition of the bird, the percentage of conservation, growth and feed costs were taken into account.

The results of the tests to determine the effectiveness of CSR when vaccinating broilers against BNK are shown in Table 8.

TABLE 8

The influence of KSO on the effectiveness of vaccination against New Castle disease

| Indicators | Control | Experience 1 | Experience 2 | Experience 3 |
|---|---|---|---|---|
| The average titer in RGA | 25 ± 3 | 45 ± 13 | 95 ± 32 | 180 ± 46* |
| Immunity Tension % | 75 | 88.6 | 100 | 100 |

Note: *P < 0.05

The average titers of specific antibodies to BNV in both the control and experimental groups were protective. However, in the study of broiler sera at 42 days of age with the use of KSO, a significant increase in the average titer in the experimental group 3 was established in comparison with the control by 6 times (<0.01). In the experimental groups (1,2), no significant difference in antibody titers was found in comparison with the control, however, they were at the protective level and a tendency to increase this indicator by 1.8 and 4.3 times was found. Group immunity in the control was 75%, while in the experimental groups (3.4) 100%, in the 1st experimental group 88.6%. The death of broilers was in the control—9.8%, while the percentage of death decreased in the experimental groups: 2.9; 4.5 and 4.4 times, respectively, in comparison with the control. The average daily gains in the experimental groups ranged from 50-55 grams, while in the control the average weight gain was 46 grams.

Thus, we can conclude that the optimal scheme for using KSO for broilers in regions with a difficult epizootic situation with BNK is to use the drug at a dose of 0.03 ml/kg live weight for 3 days before vaccination and for 7 to 10 days after vaccination against BNK. The use of the drug according to the above scheme leads to a six-fold increase in the average titer of specific antibodies to the BNK virus and 4-fold decrease in the death rate of chicken broilers.

Example 3 concerns obtainment of a supramolecular combinatorial dipyridamole mixture (CD) like binding and terminating component.

Example 3 procedure involves first diluting 222 µM of dipyridamole (I) (CAS N 58-32-2, Mr=504.636 g/mol, n=4) in 50 ml of dioxane in mixture with 50 ml of glacial acetic acid, and adding 60 µM of succinic anhydride (III) and 61 µM of acetic anhydride (II). Then the solution is stirred and warmed with a backflow condenser for 5 to 50 minutes. Then the solution is poured into vials and lyophilized to remove solvents and acetic acid to create the combinatorial mixture (IV) which is CD. The combinatorial mixture (IV) is used to make pharmaceutical compositions, to study structures, and to determine bioactivity of CD.

Figure 8:
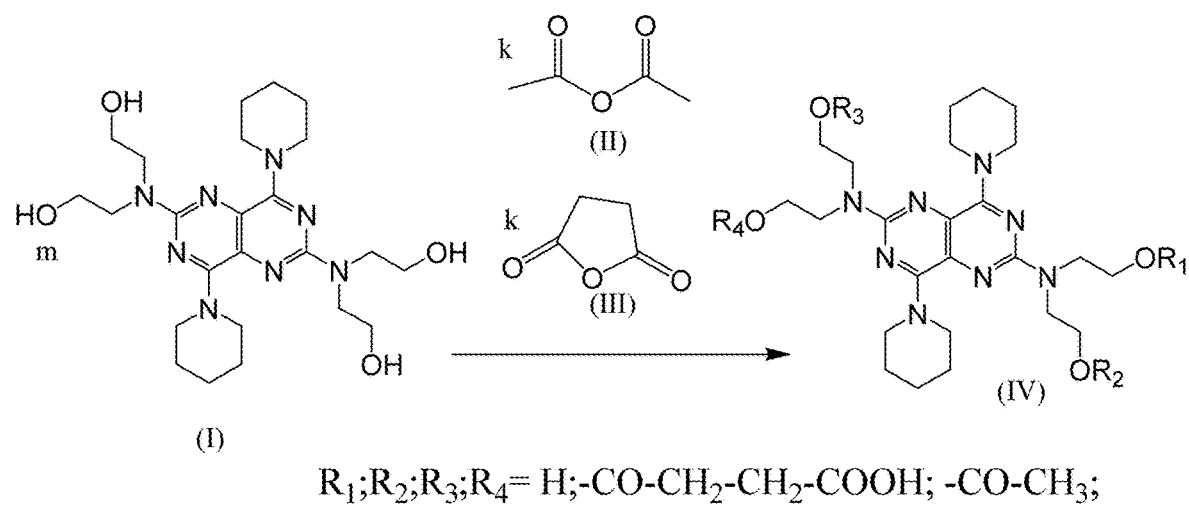
FIG. 8 depicts a scheme of combinatorial dipyridamole derivative synthesis (IV) which comprises a combinatorial reaction of dipyridamole (I) with two modifiers (II, III).

Note that FIG. 8 provides the Example 3 scheme of combinatorial dipyridamole derivatives (CD) synthesis. Instead of carboxylic acid anhydride modifiers, optionally halides of carboxylic and polycarboxylic acids, such as succinic, maleic, fumaric, lactic, propionic, other halogen derivatives, such as chloromethane, bromoethane, chloropropane, cyclic alkylating compounds like oxirane, or propiolactone may be used to make combinatorial dipyridamole derivatives.

FIG. 8 depicts one parent molecule of dipyridamole (I) which provides 4 residual hydroxyl groups that may be available for modification (n=4) to create a combinatorial mixture. The amino groups as a part of residual morpholine and the pyrimidine nucleus can be protonated and protected against modification under the given reaction conditions. Calculations of the number of modifier moles are carried out according to the combinatorics formulas: $m=4\times(3\times2^{i^2}-1)$; $k=n\times(2^n-1)$, where m is the number of different molecule derivatives in the combinatorial mixture and the number of dipyridamole moles for reaction; n is the number of hydroxyl groups available for modification in the structure of dipyridamole (n=4); k is the number of moles of each modifier. Thus, having only one parent dipyridamole molecule and two modifiers after combinatorial synthesis, we in theory will obtain 12 combinatorial derivatives with different degrees of substitution, different positions of the substituents and different shuffling of the modifier residues. This is not a simple mixture, but a difficult to separate supramolecular mixture. Due to the presence of both substituted and non-substituted hydroxyl groups in the different derivatives, the supramolecular structures will be formed through both hydrogen and ionic bonds, including with tertiary amino groups of heterocycles.

Optionally, in some embodiments of the present invention, modifiers, such as either succinic anhydride or acetic anhydride can be used and introduced both simultaneously and sequentially, or optionally succinic anhydride can be first introduced and warmed in the mixture using a backflow condenser, and then acetic anhydride can be introduced and the mixture reheated. Similarly, by this synthesis approach, instead of using succinic anhydride as a modifier, other embodiments of the present invention are contemplated by alternative synthetic approaches which employ related chemical modifiers including for example, anhydrides such as maleic anhydride, aconitic anhydride, glutaric, or phthalic anhydride; acids such as for example, acetic anhydride, ethyl formic acid, or monochloroacetic acid; and various alkylating agents including for example propiolactone, ethylene oxide, methyl chloride, ethyl chloride, or propyl chloride.

NMR $C^{13}$ (carbon-13-nuclear magnetic resonance) was performed on the combinatorial dipyridamole derivatives (CD). The results were C: 96, 1; 161, 8; 170, 0; 157, 8; $CH_2$: 58, 9; 61, 7; 58, 1; 61, 4; 29, 2; 29, 1; CO: 173, 1; 174, 7; 170, 2; and $CH_2$ (in morpholine cycle) 52, 7; 25, 4; 25, 5. The $C^{13}$ NMR data of the combinatorial derivative confirms the presence of both ethyl groups of succinic acid residues in its CD structure and acetyl residues as reaction products with the modifier acetic anhydride.

HPLC was performed using an HPLC column (Milichrom A-02 microcolumn chromatograph with a gradient of acetonitrile (5-100%)/0.1 M chloric acid and 0.5 M lithium perchlorate). The CD in the HPLC chromatogram displayed one clear, broadened peak and was not separated into components, although the retention time differed from both the starting dipyridamole and its completely substituted derivatives. The complex supramolecular structures formed between the 12 different combinatorial derivatives of the CD were not be separated chromatographically by this HPLC column method. Similarly, this combinatorial dipyridamole derivative (CD) was not separated using thin layer chromatography (TLC) that used a as a mobile phase acetonitrile:water and used UV detection. The CD TLC showed only a single band which did not coincide with any of the obtained derivatives.

Figure 9:
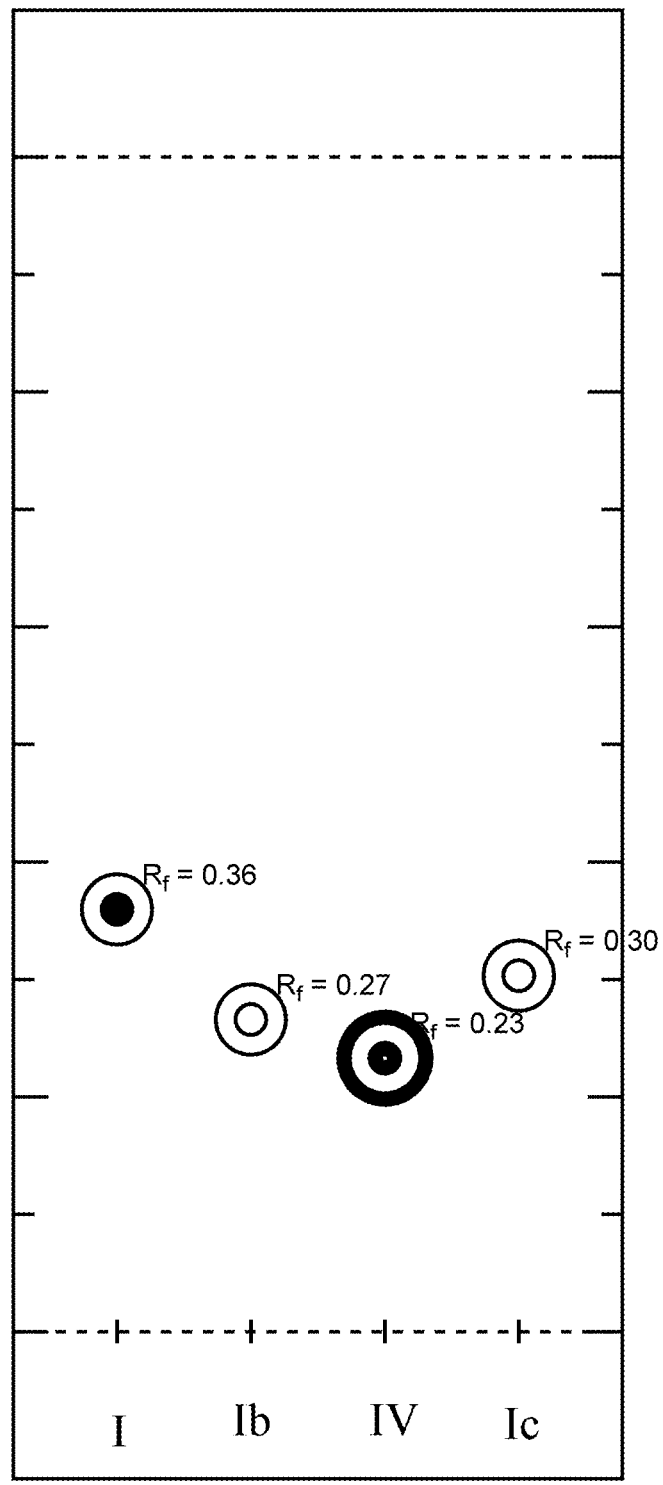
FIG. 9 presents a thin-layer chromatogram of combinatorial dipyridamole derivative (IV), an initial dipyridamole (I), a completely acylated dipyridamole (Ib) and a completely succinylated dipyridamole (Ic).

In FIG. 9 depicted is a TLC of the combinatorial mixture (IV) which is less mobile, and with the initial unmodified dipyridamole (I) the lightest TLC band. Completely acylated dipyridamole (Ib) and succinylated dipyridamole (Ic) TLC bands appear in between the TLC bands of the native dipyridamole and the dipyridamole combinatorial. Also, the combinatorial dipyridamole band was not separated into its complex supramolecular structures by using two-dimensional TLC or by using HPLC (data not shown).

A study was conducted to test inhibition of a cAMP-phosphodiesterase by various supramolecular combinatorial dipyridamole derivatives. The various supramolecular combinatorial dipyridamole derivatives were obtained in the synthesis reactions by using different molar ratios of the modifiers. A cyclic AMP solid-phase sandwich ELISA (enzyme-linked immunosorbent assay) was used. The reaction was stopped by the addition of a double volume of 1% TCA.

TABLE 9

Inhibiting property regarding cAMP-phosphodiesterase (PDE) from supramolecular combinatorial derivatives of dipyridamole obtained in the reaction with different molar ratio of modifiers

| Item No. | Reagent molecular ratio* | | | $ED_{50}$ as related to cAMP, µg/ml, measuring error 10% |
|---|---|---|---|---|
| | m | k1 | k2 | |
| 1 | 44 | 88*** | 88*** | >500 |
| 2 | -//- | 70 | 70 | 100 |
| 3 | -//- | 61 | 60 | 0.01 |
| 4 | -//- | 30 | 30 | 5 |
| 5 | -//- | 15 | 15 | 10 |
| 6 | -//- | 7 | 7 | 60 |
| 7 | -//- | 3 | 3 | 115 |
| 8 | -//- | 2 | 2 | 210 |
| 9 | -//- | 1 | 1 | 300 |
| 10 | -//- | 0 | 0 | 300 |

*m - number of moles of dipyridamole in the combinatorial synthesis reaction;
k1 - number of moles of succinic anhydride in the reaction;
k2 - number of moles of acetic anhydride in the reaction;
**$ED_{50}$µg/ml of PDE inhibition was determined by diluting the initial concentration of the dipyridamole derivative;
***maximum molar ratio at which all groups in dipyridamole are replaced, exceeding this ratio leads to the fact that in the reaction unreacted modifiers - succinic anhydride and acetic anhydride remain in medium.

Above Table 9 presents experimental data which taken as a whole reveals unexpected enzymatic inhibition potency utilities for some embodiments of the present invention. It can be seen from Table 9, Item No. 3, that the $ED_{50}$ for inhibition of cAMP phosphodiesterase by supramolecular combinatorial dipyridamole derivatives is lowest (0.01 ug/ml $ED_{50}$) when the molar ratio of the three reagent modifiers (m, k1, and k2) is 44:61:60. Note that with m at 44, a rather slight lowering of molar ratio amounts of k1 and k2 from 70,70 to 60,61 causes a surprising 10,000 fold improvement in cAMP phosphodiesterase inhibition. What would have been expected by teachings in the prior art concerning synthetic organic chemistry by one of a high level of skill in this art would very slight alteration in the amounts of modification of the derivatization of the supramolecular combinatorial dipyridamole derivatives. Furthermore, it is also surprising and unexpected that in relation to molar amount of reagent m, that a further lowering of k1 and k2 reagent ratios from 60,61 to only 30,30 would result in a 500-fold loss in potency of the supramolecular combinatorial dipyridamole derivatives in terms of their ability to inhibit a cAMP phosphodiesterase. This invention discovery clearly demonstrates the exquisite sensitivity and unexpected utility of the present invention synthesis processes for making supramolecular combinatorial derivatives of dipyridamole as well the non-obviousness of the compounds comprising the supramolecular combinatorial derivatives of dipyridamole. In addition, it is noteworthy to note that Table 9, Items No. 1 and 10 indicate that the most low potency inhibitors of cAMP phosphodiesterase are the supramolecular combinatorial derivatives of dipyridamole that have been either maximally or that have been minimally modified by k1 and k2 reagents in presence of a fixed amount of reagent m. In summary, the synthetic chemical product combinatorial compositions and their synthesis details presented in Table 9 as Items No. 1 thru Item No. 9 have been found to have unexpected variations in usefulness as a cAMP phosphodiesterase inhibitor.

The following Table 10 shows the formulations of the studied pharmaceutical compositions (FC, CD).

TABLE 10

Formulation and ratio of ingredients of the pharmaceutical composition (FC CD) per capsule or pill

| Item No. | Ingredient name | % |
|---|---|---|
| 1 | 2 | 3 |
| 1. | CD | 0.1-20.0 |
| 2. | Papaverine | 0.5-10.0 |
| 3. | Ascorbic acid | 0.2-10.0 |
| 4. | Bendazole | 0.5-10.0 |
| 5. | Tadalafil | 1-5.0 |
| 6. | Sodium valproate | 5-20.0 |
| 7. | Excipients | up to 100% |

As a control, the animals were applied the same composition with the same substances (in the form of Carbopol gel), but without CD (FC).

Sample 3 concerns combinatorial base amino acids and base oligopeptide as binding component. KKRKRKRKR Oligopeptide Combinatorial Mixture is hereinafter abbreviated as KR. Preliminarily, the KKRKRKRKR oligopeptide is prepared using a standard peptide synthesizer technique or by a genetic engineering method. The procedure is as follows: 1 Mmol of KKRKRKRKR oligopeptide is dissolved in 50 ml of phosphate buffered saline, and then 3 Mmol of succinic anhydride and 3 Mmol of phthalic anhydride are added, and the solution is stirred until both anhydrides are completely dissolved. The solution is poured into vials, lyophilized and used for analysis and research. The calculation of the molar ratios of two modifiers to the oligopeptide is carried out according to the formulas:
(1) k=n×(2n−1) and (2) m=4×(3×2n−2−1). The n=number of substitutional groups in the oligopeptide (n=9). The m=the number of moles of the original oligopeptide. The number of different molecules of its combinatorial derivatives after synthesis from the same source peptide is 1532 different derivatives based on these calculations given the places of substitutions and in permutations. The k=the number of moles of each of the two modifiers in the combinatorial synthesis reaction to obtain the maximum number of different derivatives (k=4599). In this example, the molar ratio to obtain the maximum number of different derivatives (1532 different molecules) is 3:3:1 (succinic anhydride: phthalic anhydride: KKRKRKRKR oligopeptide).

Figure 10:
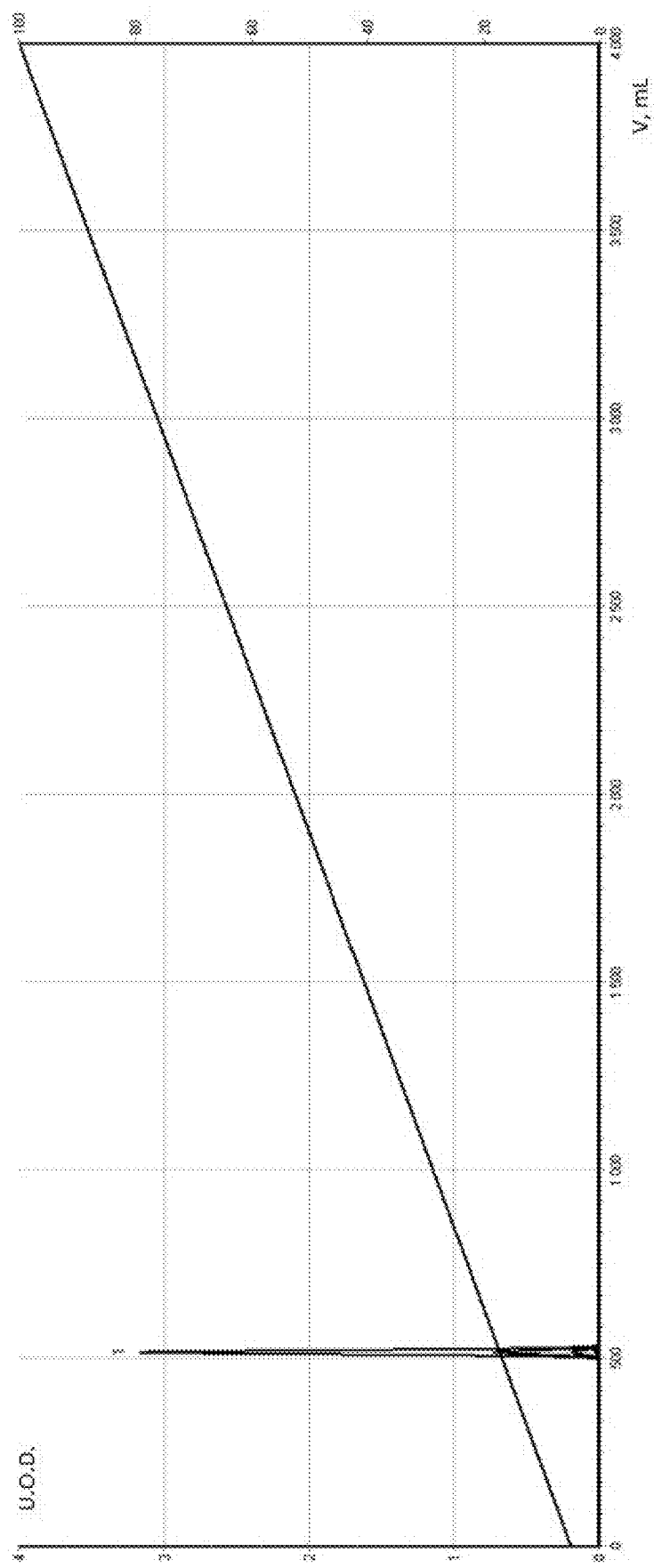
FIG. 10 presents a result of an HPLC analysis of a starting peptide KKRKRKRKR. The starting peptide when detected at 280 nm wavelength yields one absorption band.
Figure 11:
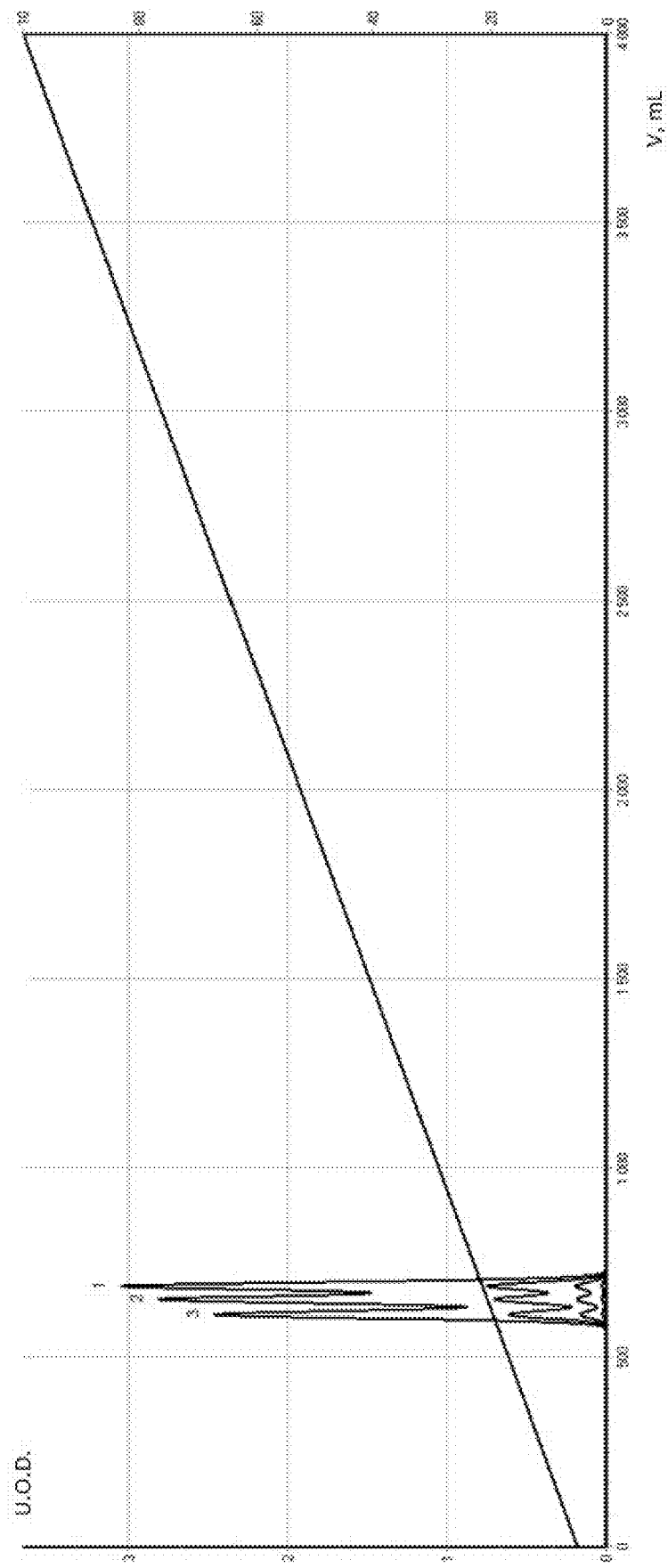
FIG. 11 presents a result of an HPLC analysis of a combinatorial derivative peptide KKRKRKRKR. The chromatogram of the peak of the combinatorial derivative peptide KKRKRKRKR is shifted to a location expected for a more hydrophilic peptide, is still broadened, and is divided into 3 additional bands.
Figure 12:
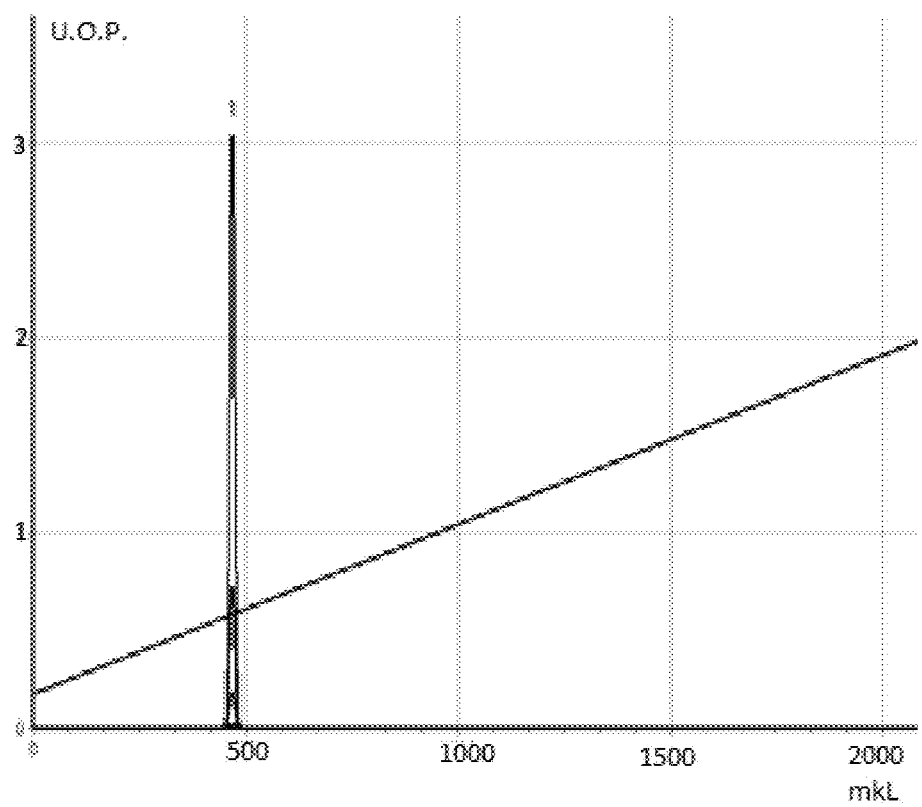
FIG. 12 presents an HPLC analysis of the original peptide KKRKSTRKR. The original peptide when using the detector in the region of 280 nm gives one absorption band.
Figure 13:
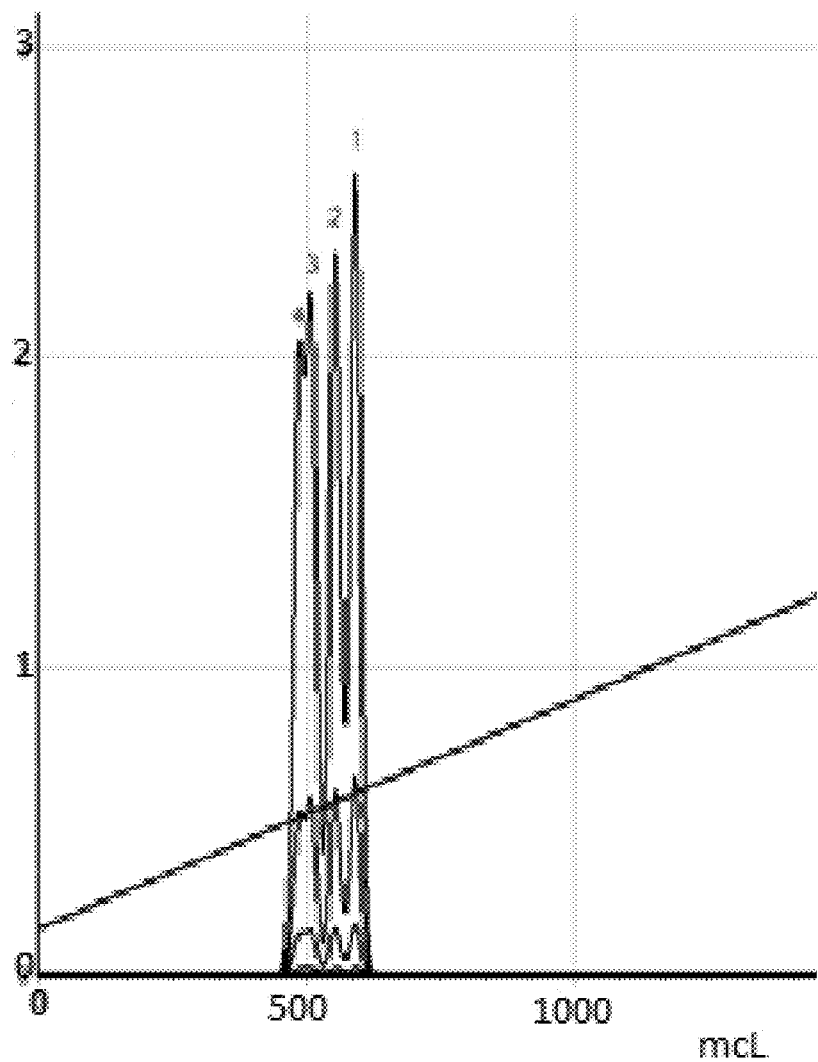
FIG. 13 presents a result of an HPLC analysis of the combinatorial derivative peptide KKRKSTRKR and the chromatogram has a triple peak.

FIG. 10 shows the result of HPLC analysis of the starting peptide KKRKRKRKR. The original peptide when using the detector in the region of 280 nm gives one absorption band. FIG. 11 shows the result of HPLC analysis of the combinatorial derivative peptide KKRKRKRKR. As can be seen from the chromatogram, the peak of the peptide is not only located in another place—in the region of a more hydrophilic region, it is still broadened, divided into 3 additional bands. The HPLC data suggests that among the 1532 different derivatives of the peptide, there are ionic and hydrogen intramolecular/supramolecular bonds which are not broken during the HPLC instrument separation process under classical gradient HPLC conditions. Using thin-layer chromatography and capillary gel electrophoresis, it was also not possible to separate the supramolecular derivatives into separate fragments.

Optional modifications to the peptide, other combinations of at least two different modifiers can be used, wherein the modifiers are carboxylic and polycarboxylic acid anhydrides, carboxylic acid halides, and/or halocarbons. The peptide modified may by one individual oligopeptide or oligopeptide mixtures. Peptides can be obtained by standard methods including using peptide synthesizers, genetic engineering methods, and/or using recombinant technology methods known in the prior art.

To check the biological (antiviral) activity of the synthesized derivatives with different ratios of components in the combinatorial synthesis reaction, the antiviral activity of the derivatives was studied by the screening method on models of the H1N1 influenza virus (Inf), the reference strain of vesicular stomatitis virus (Vesic.—VVS) and type 1 herpes virus (Herp.—strain L-2) in table on chicken fibroblast culture according to the degree of degradation (cytopathic effect, detachment from the bottom of the hole). The degree of "degradation" cells was determined by staining the culture with a vital dye, the concentration of which was determined spectrophotometrically with respect to a healthy monolayer and an empty well. The results of in vitro studies are shown in Table 11 below.

TABLE 11

Antiviral activity of supramolecular combinatorial derivatives of the oligopeptide KKRKRKRKR obtained in the reaction with different molar ratio of modifiers

| | The molar ratio of reagents * | | | % cytoprotective antiviral activity ** | | |
|---|---|---|---|---|---|---|
| No | m | k1 | k2 | Inf | Herp | Vesic |
| 1 | 1532 | 18396 *** | 1 | 0 | 0 | 0 |
| 2 | 1532 | 9198 | 4 | 0 | 0 | 0 |
| 3 | -//- | 4599 | 9 | 0 | 0 | 0 |
| 4 | -//- | 2299 | 18 | 0 | 0 | 0 |
| 5 | -//- | 1149 | 36 | 0 | 0 | 0 |
| 6 | -//- | 575 | 72 | 0 | 0 | 0 |
| 7 | -//- | 287 | 143 | 0 | 0 | 0 |
| 8 | -//- | 143 | 287 | 0 | 0 | 0 |
| 9 | -//- | 72 | 575 | 0 | 0 | 0 |
| 10 | -//- | 36 | 1149 | 0 | 0 | 0 |
| 11 | -//- | 18 | 2299 | 0 | 0 | 0 |
| 12 | -//- | 9 | 4599 | 0 | 0 | 0 |
| 13 | -//- | 1 | 9198 | 0 | 0 | 0 |
| 14 | -//- | 0 | 18396 *** | 0 | 0 | 0 |
| 16 | -//- | 9198 *** | 9198 *** | 0 | 0 | 0 |
| 17 | -//- | 4599 | 4599 | 100 | 100 | 100 |
| 18 | -//- | 2299 | 2299 | 50 | 50 | 50 |
| 19 | -//- | 1149 | 1149 | 25 | 25 | 25 |
| 20 | -//- | 575 | 575 | 0 | 0 | 0 |
| 21 | -//- | 287 | 287 | 0 | 0 | 0 |
| 22 | -//- | 143 | 143 | 0 | 0 | 0 |
| 23 | -//- | 72 | 72 | 0 | 0 | 0 |
| 24 | -//- | 36 | 36 | 0 | 0 | 0 |
| 25 | -//- | 18 | 18 | 0 | 0 | 0 |
| 26 | -//- | 9 | 9 | 0 | 0 | 0 |
| 27 | -//- | 1 | 1 | 0 | 0 | 0 |
| 28 | -//- | 18396 | 0 | 0 | 0 | 0 |
| 29 | -//- | 9198 *** | 0 | 0 | 0 | 0 |
| 30 | -//- | 4599 | 0 | 0 | 0 | 0 |
| 31 | -//- | 2299 | 0 | 0 | 0 | 0 |
| 32 | -//- | 1149 | 0 | 0 | 0 | 0 |
| 33 | -//- | 575 | 0 | 0 | 0 | 0 |
| 34 | -//- | 287 | 0 | 0 | 0 | 0 |
| 35 | -//- | 143 | 0 | 0 | 0 | 0 |
| 36 | -//- | 72 | 0 | 0 | 0 | 0 |
| 37 | -//- | 36 | 0 | 0 | 0 | 0 |
| 38 | -//- | 18 | 0 | 0 | 0 | 0 |
| 39 | -//- | 9 | 0 | 0 | 0 | 0 |
| 40 | -//- | 1 | 0 | 0 | 0 | 0 |
| 41 | -//- | 0 | 18396 *** | 0 | 0 | 0 |
| 42 | -//- | 0 | 9198 | 0 | 0 | 0 |
| 43 | -//- | 0 | 4599 | 0 | 0 | 0 |
| 44 | -//- | 0 | 2299 | 0 | 0 | 0 |
| 45 | -//- | 0 | 1149 | 0 | 0 | 0 |
| 46 | -//- | 0 | 575 | 0 | 0 | 0 |
| 47 | -//- | 0 | 287 | 0 | 0 | 0 |
| 48 | -//- | 0 | 143 | 0 | 0 | 0 |
| 49 | -//- | 0 | 72 | 0 | 0 | 0 |
| 50 | -//- | 0 | 36 | 0 | 0 | 0 |
| 51 | -//- | 0 | 18 | 0 | 0 | 0 |

TABLE 11-continued

Antiviral activity of supramolecular combinatorial derivatives of the oligopeptide KKRKRKRKR obtained in the reaction with different molar ratio of modifiers

| | The molar ratio of reagents * | | | % cytoprotective antiviral activity ** | | |
|---|---|---|---|---|---|---|
| No | m | k1 | k2 | Inf | Herp | Vesic |
| 52 | -//- | 0 | 9 | 0 | 0 | 0 |
| 53 | -//- | 0 | 1 | 0 | 0 | 0 |
| 54 | -//- | 0 | 0 | 0 | 0 | 0 |

* m is the number of moles of the KKRKRKRKR oligopeptide in the combinatorial synthesis reaction; K1 is the number of moles of succinic anhydride in the reaction; K2 is the number of moles of phthalic anhydride in the reaction;

** % of the remaining monolayer of cells after infection with viruses and replacing the culture with the studied drug in the culture after 48 hours of incubation in the presence of the test substance added in a pre-selected concentration (ED90 = 0.05 µg /ml);

*** the maximum molar ratio at which all groups in the oligopeptide are replaced, an excess of this ratio leads to the fact that unreacted modifiers remain in the reaction medium - succinic anhydride and phthalic anhydride.

As can be seen from the Table 11, a dose of 0.05 ug/ml of supramolecular structure derivative No. 17 (KR) completely protected a cell monolayer (ED100) from degrading cytopathic agents effect of viruses. The calculated molar ratio of reagents for derivative No. 17 is reagent m=1532, reagent k1=4599 and reagent k2=4599. This molar ratio of the three reagents caused a formation of the maximum number of different oligopeptide derivatives (see footnotes to Table 11.)

Synthesis of Combinatorial Mixture of Oligopeptide KKRKSTRKR (called KR2)

Preliminarily, the KKRKSTRKR oligopeptide KR2 is prepared using a standard peptide synthesizer technique or by genetic engineering.

1 Mm of KKRKSTRKR oligopeptide is dissolved in 50 ml of phosphate buffered saline, 3 Mm of succinic anhydride and 3 Mm of maleic anhydride are added, and the solution is stirred until both anhydrides are completely dissolved. The solution is poured into vials, lyophilized and used for analysis and research. The calculation of the molar ratios of two modifiers to the oligopeptide is carried out according to the formulas: (1) $k=n\times(2n-1)$ (2) $m=4\times(3\times2n-2-1)$ where: n=number of substitutional groups in the oligopeptide (n=9); m=the number of moles of the original oligopeptide and the number of different molecules of its combinatorial derivatives after synthesis (from the same source peptide, 1532 different derivatives are formed both in the places of substitutions and in permutations); and k=the number of moles of each of the two modifiers in the combinatorial synthesis reaction to obtain the maximum number of different derivatives (k=4599). In this case, the molar ratio to obtain the maximum number of different derivatives (1532 different molecules) is 3:3:1 (succinic anhydride: phthalic anhydride: KKRKSTRKR oligopeptide).

FIG. 12. shows the result of HPLC analysis of the original peptide KKRKSTRKR. The original peptide when using the detector in the region of 280 nm gives one absorption band. FIG. 13 shows the result of HPLC analysis of the combinatorial derivative peptide KKRKSTRKR. As can be seen from the chromatogram, the peak of the peptide is not only located in another place—in a more hydrophilic region, it is still broadened, divided into 4 additional bands. This suggests that between 1532 different derivatives of the peptide there are intramolecular/supramolecular bonds of ionic and hydrogen nature, which are not able to be broken during the HPLC separation under classical gradient HPLC conditions. Using thin-layer chromatography and capillary gel electrophoresis, it was also not possible to separate the supramolecular derivative into separate fragments. To modify the peptide, other combinations of at least two different modifiers can be used: carboxylic and polycarboxylic acid anhydrides, carboxylic acid halides, halocarbons. As peptides, one individual oligopeptide can be used as well as oligopeptide mixtures obtained both by the standard method using peptide synthesizers and by genetic engineering methods and using recombinant technology.

The following types of transplantable cells of human and animal origin were used to determine the maximum tolerated concentration (MIC) in toxicological experiments and study the antiviral activity of the drug KR: PT, Tr, Ner-2, Hela, and chicken embryos. Note that PT are transplantable cells of the kidney of the cattle embryo. Tr are tracheal cells of the cattle embryo. Ner-2 are transplantable cells of human larynx cancer. Hela are transplantable cancer cells of the uterus. Chicken embryos Cells were grown in 199 medium supplemented with 10% bovine serum and antibiotics (penicillin and streptomycin). Influenza viruses (H3N2), vesicular stomatitis (Indiana strain), coronavirus (X 343/44) and herpes simplex virus type 1 (strain L-2) were used as test viruses.

The antiviral effect of the drug KR2 was studied on influenza A virus (H3 N2).

Aqueous solutions of KR2 in various doses (ten-fold dilutions) were administered to 15 chicken embryos in the allantoic cavity in a volume of 0.2 ml at a time which was 12 hours after the virus was introduced in a working dose (100 TCD50/0.2 ml). Each experiment was accompanied by control of the test virus in the working dose. Infected and non-infected (control) embryos were incubated at 36° C. for 48 hours. Then, the embryos were opened, from which the allantoic fluid was aspirated. Titration of the virus in allantoic fluid was carried out according to the generally accepted method with 1% red blood cells of 0 (1) human blood group. Defined coefficient of protection (KZ). The virus titer in the experimental and control groups of chicken embryos is presented in Table 12.

TABLE 12

Effective concentration of KR2 in a model of influenza infection in Ovo

| Group | The concentration of the drug (mg/ml) | Virus titer ($lg\ TCA_{50/mL}$) experiment | control | Minimum effective concentration (MEC mg/mL) |
|---|---|---|---|---|
| Control (0.9% sodium chloride solution was injected) | — | 12 | 12 | — |
| Experimental | 50 ± 5 | 0 | 12 | |
| | 5 ± 1 | 0 | 12 | 0.05 |
| | 0.5 ± 0.05 | 2 | 12 | |
| | 0.05 ± 0.005 | 4 | 12 | |
| | 0.005 ± 0.0005 | 6 | 12 | 5 |

As can be seen from Table 12, the minimum effective concentration of KR2 against influenza virus, which completely inhibits the synthesis of the virus, is 0.05 mg/ml. With increasing dilution of the drug, the effectiveness of KR2 decreases and has a dose-dependent character. This fact indicates the presence of a direct antiviral effect of the drug KR2 in relation to the H3N2 influenza virus.

The study of the antiviral effect of the drug KR on cytopathic viruses (vesicular stomatitis virus, coronavirus, herpes simplex virus type 1) Antiviral activity against this viruses group was determined in a culture of the above cells. The reaction was carried out in the following way: 0.2 ml of the corresponding virus in a working dose (100 TCD50/0.2 ml) was added in a volume of 0.2 ml in a 2-day washed cell culture. 0.8 ml of support medium was added. When the CPP appeared in the culture, the drug KR was introduced in various doses. As a control, the same was done with test viruses without the drug. Cells were incubated at 37° C. in an incubator. The experience was recorded on 3.5.7 days. The decrease in virus titer under the influence of the test drug by 2 lg or more in comparison with the control was evaluated as a manifestation of antiviral activity. The results of a study of the antiviral activity of the drug KR2 are presented in Table 13.

TABLE 13

The study of the antiviral effect of the drug KR2 against viruses: vesicular stomatitis, coronavirus, herpes simplex virus type 1)

| Drug | Virus | MEC, mg/mL | Maximum drop in virus titer, $lg\ TCA_{50/mL}$ |
|---|---|---|---|
| KR2 | VSV | 0.05 | 3.9 |
| | CV | 0.05 | 2.9 |
| | HSV1 | 0.05 | 4.9 |

As can be seen from Table 13, KR2 has antiviral activity and the ability to suppress the reproduction of all the viruses studied by us at a concentration of 0.05 mg/ml with MEC=50 μg/ml. The CTI of the drug is 1000. In addition, KR2 was active against all the viruses studied, while no comparison drug showed such activity. Thus, the drug is not associated with specific characteristics of the virus or cell culture but affects the mechanisms common to all cells.

Aspects of the invention include supramolecular structures, also called supramolecular soluble nanoparticles (SNPs), having a) a plurality of binding components, each having a plurality of binding regions, wherein the plurality of binding regions comprises combinatorial carboxylated cobalamins; b) a plurality of cores that are suitable to at least provide some mechanical structure to said self-assembled supramolecular soluble systems, wherein each of said plurality of cores is an organic core, which comprises at least one core binding element adapted to bind to the binding regions to form a first inclusion complex, wherein the core binding element comprises combinatorial carboxylated dipyridamole, and wherein the first inclusion complex is combinatorial carboxylated cobalamin with combinatorial carboxylated dipyridamole; c) a plurality of terminating components, each having a single terminating binding element that binds to remaining binding regions of one of said plurality of binding components by forming a second inclusion complex, wherein the single terminating binding element comprises combinatorial carboxylated dipyridamole, and wherein the second inclusion complex is combinatorial carboxylated dipyridamole; d) plurality of cores and plurality of binding components are self-assembled carboxylated base-amino acids—lysine, histidine and arginine, and assemble when brought into contact to form self-assembled supramolecular soluble systems, and e) plurality of terminating components act to occupy the remaining binding regions of plurality of binding components, and plurality of terminating components are present in a sufficient quantity relative to plurality of binding regions of plurality of binding components to terminate further binding, thereby forming a discrete particle.

The structural components and binding components of some embodiments of the present invention comprising supramolecular structures, also called supramolecular soluble nanoparticles (SNPs) can self-assemble when brought into contact to form a supramolecular structure. The terminating components can act to occupy binding regions of the binding components to terminate further binding when the terminating components are present in a sufficient quantity relative to the binding regions of the binding components. In some embodiments, the structural component comprises a plurality of binding elements that bind to the binding regions of the binding components. In some embodiments, the terminating component has a single binding element that binds to one binding region on one binding component. In some embodiments, the supramolecular structure has at least two or more different terminating components.

In some embodiments of the present invention, the binding regions (on the binding component) can bind to the terminating components or structural components so as to form a molecular recognition pair. In some embodiments, at least one structural component, at least one binding components, or at least one terminating component has a functional element. In some embodiments, the supramolecular structure has two or more different functional elements.

In some embodiments, the invention is a composition of matter comprising supra-molecular structures, also called supramolecular soluble nanoparticles (SNPs) comprising a mixture of combinatorial carboxylated cobalamins comprising for example, a mixture of a succinylated derivative of cyanocobalamin, a cyanocobalamin, a methyl cobalamin, a hydroxycobalamin, and/or a cobamid.

In other embodiments of the invention, the invention is a composition of matter comprising supramolecular structures, also called supramolecular soluble nanoparticles (SNPs) comprising a mixture of combinatorial carboxylated cobalamins comprising a succinylated hydroxycobalamin, a succinylated cobamid, a succinylated methyl cobalamin and/or a succinylated cyanocobalamin.

In yet other embodiments of the invention, the invention is a composition of matter comprising supramolecular structures, also called supramolecular soluble nanoparticles (SNPs) comprising a mixture of supramolecular combinatorial carboxylated riboflavins comprising supramolecular combinatorial succinylated derivatives of riboflavins, flavin mononucleotide, and/or flavin dinucleotide.

In yet other embodiments of the invention, the invention is a composition of matter comprising supramolecular structures, also called supramolecular soluble nanoparticles (SNPs) comprising a mixture of combinatorial carboxylated dipyridamoles comprising supramolecular succinylated combinatorial dipyridamole derivatives; supramolecular maleylated combinatorial dipyridamole derivatives, and/or carboxymethylated combinatorial dipyridamole derivatives.

In yet other embodiments of the invention, the invention is a composition of matter comprising supramolecular structures, also called supramolecular soluble nanoparticles (SNPs) comprising supramolecular structures further comprising carboxylated basic amino acids such as lysine, histidine and arginine, and may include bis-succinylated, maleylated and carboxymethylated amino acid derivatives of carboxylated basic amino acids such as lysine, histidine and arginine.

In yet other embodiments of the invention, the invention is a composition of matter wherein a terminating component may comprises at least one of polyethylene glycol, polymer, polypeptide, or oligosaccharide and organic core comprises at least one of a dendrimer, branched polyethyleneimine, linear polyethyleneimine, polyline, polylactide, polylactide-co-glycoside, polyanhydrides, poly-ε-caprolactones, polymethyl methacrylate, poly (N-isopropyl acrylamide) or polypeptides.

In yet other embodiments of the invention, the invention is a composition of matter wherein a binding component further comprises a combinatorial carboxylated derivatives of basic oligopeptide KKRKRKRKR, their carboxylated derivatives in form succinylated, maleylated and carboxymethylated derivatives in mixture with one another. Also, the binding and terminated component can be used poly-L-lysine.

Support for original claims of present invention embodiments includes below text.

Support for claim 1: Supramolecular nanoparticles, comprising: a combination of nanostructures selected from the group consisting of combinatorial carboxylated cobalamins obtained from a first combinatorial synthesis; combinatorial carboxylated dipyridamoles obtained from a second combinatorial synthesis; basic amino acid polypeptides obtained from a third combinatorial synthesis, and any combination thereof.

Support for claim 2: The supramolecular nanoparticles according to claim 1, wherein the supramolecular nanoparticles have antiviral properties, wherein the supramolecular nanoparticles further comprise dynamic self-organizing soluble nanostructures, and wherein the nanostructures further comprise a plurality of binding components; a plurality of organic cores; and a plurality of terminating components.

Support for claim 3: The supramolecular nanoparticles according to claim 2, wherein one of the binding components further comprises combinatorial carboxylated cobalamins which have a number of binding regions, wherein the organic cores further comprise the combinatorial carboxylated dipyridamoles which have at least one binding element adapted for binding to the combinatorial carboxylated cobalamins, wherein the organic cores further comprise mechanical structures for the dynamic self-organizing soluble nanostructures, and wherein the binding of the combinatorial carboxylated cobalamins to the combinatorial carboxylated dipyridamoles can further comprise first inclusion complexes.

Support for claim 4: The supramolecular nanoparticles according to claim 3, wherein the terminating components each have at least one terminating binding element that binds to a remaining binding region of one of the binding components and can further comprise second inclusion complexes.

Support for claim 5: The supramolecular nanoparticles according to claim 4, wherein the basic amino acid polypeptides further comprise carboxylated basic amino acids of basic amino acids selected from the group consisting of lysine, histidine, arginine, derivatized lysine, derivatized histidine, derivatized arginine, acylated lysine, acylated histidine, acylated arginine, and any combination of basic amino acids thereof.

Support for claim 6: The supramolecular nanoparticles according to claim 5, wherein the plurality of terminating components occupy the remaining binding regions of the plurality of binding components, wherein the plurality of terminating components are in a quantity relative to the plurality of the binding regions of the plurality of the binding components so as to terminate further binding of binding components, wherein the supramolecular nanoparticles further comprise discrete nanoparticles based on the dynamic self-organizing soluble nano structures.

Support for claim 7: The supramolecular nanoparticles according to claim 1, wherein the combinatorial carboxylated cobalamins are a succinylated cyanocobalamins mixture.

Support for claim 8: The supramolecular nanoparticles according to claim 1, wherein combinatorial carboxylated cobalamins are a succinylated methyl cobalamins mixture.

Support for claim 9: The supramolecular nanoparticles according to claim 1, wherein combinatorial carboxylated cobalamins are a succinylated hydroxycobalamins mixture.

Support for claim 10: The supramolecular nanoparticles according to claim 1, wherein combinatorial carboxylated cobalamins are a succinylated cobamides mixture.

Support for claim 11: The supramolecular nanoparticles according to claim 1, wherein combinatorial carboxylated cobalamins are selected from the group consisting of succinylated hydroxycobalamins mixtures, succinylated cobamides mixtures, succinylated hydroxycobalamins mixtures, succinylated methyl cobalamins mixtures, succinylated cyanocobalamins mixtures, and any combination thereof.

Support for claim 12: The supramolecular nanoparticles according to claim 2, wherein at least one of the organic cores further comprises at least one element selected from a photo-dynamic component which is supramolecular combinatorial carboxylated riboflavins.

Support for claim 13: The supramolecular nanoparticles according to claim 12, wherein the supramolecular combinatorial carboxylated riboflavins are supramolecular combinatorial succinylated riboflavins.

Support for claim 14: The supramolecular nanoparticles according to claim 12, wherein the supramolecular combinatorial carboxylated riboflavins are supramolecular combinatorial succinylated flavin mononucleotides.

Support for claim 15: The supramolecular nanoparticles according to claim 12, wherein the supramolecular combinatorial carboxylated riboflavins are supramolecular combinatorial succinylated flavin dinucleotides.

Support for claim 16: The supramolecular nanoparticles according to claim 1, wherein the combinatorial carboxylated dipyridamoles are supramolecular succinylated combinatorial dipyridamoles.

Support for claim 17: The supramolecular nanoparticles according to claim 1, wherein the combinatorial carboxylated dipyridamoles are supramolecular maleylated combinatorial dipyridamoles.

Support for claim 18: The supramolecular nanoparticles according to claim 1, wherein the combinatorial carboxylated dipyridamoles are supramolecular carboxymethylated combinatorial dipyridamoles.

Support for claim 19: The supramolecular nanoparticles according to claim 5, wherein the carboxylated basic amino acids are selected from the group consisting of succinylated lysine, succinylated histidine, succinylated arginine, and any combination thereof..

Support for claim 20: The supramolecular nanoparticles according to claim 5, wherein carboxylated basic amino acids are selected from the group consisting of maleylated lysine, maleylated histidine, maleylated arginine, and any combination thereof.

Support for claim 21: The supramolecular nanoparticles according to claim 5, wherein carboxylated basic amino acids are selected from the group consisting of carboxymethylated lysine, carboxymethylated histidine, carboxymethylated arginine, and any combination thereof.

Support for claim 22: The supramolecular nanoparticles according to claim 5, wherein carboxylated basic amino acids are selected from the group consisting of carboxymethylated lysine, carboxymethylated histidine, carboxymethylated arginine, succinylated lysine, succinylated histidine, succinylated arginine, maleylated lysine, maleylated histidine, maleylated arginine, and any combination thereof.

Support for claim 23: The supramolecular nanoparticles according to claim 4, wherein the plurality of the terminating components comprise at least one terminating component selected from the group consisting of a polyethylene glycol, a polymer, a polypeptide, a oligosaccharide, and any combination thereof..

Support for claim 24: The supramolecular nanoparticles according to claim 3, wherein the organic cores comprise at least one organic core selected from the group consisting of a dendrimer, a branched polyethyleneimine, a linear polyethyleneimine, a polylysine, a polylactide, apolylactide-co-glycoside, a polyanhydride, a poly-ε-caprolactone, a polymethyl methacrylate, a poly (N-isopropyl acrylamide), and a polypeptide, and any combination thereof.

Support for claim 25: The supramolecular nanoparticles according to claim 2, wherein at least one of the plurality of the binding components further comprises combinatorial carboxylated derivatives of the basic oligopeptide KKRKRKRKR.

Support for claim 26: The supramolecular nanoparticles according to claim 25, wherein the combinatorial carboxylated derivatives of the basic oligopeptide KKRKRKRKR are derivatives which are succinylated on between 1 to 9 of the free amino group residues of the basic oligopeptide KKRKRKRKR.

Support for claim 27: The supramolecular nanoparticles according to claim 25, wherein the combinatorial carboxylated derivatives of basic oligopeptide KKRKRKRKR are derivatives which are maleylated on between 1 to 9 of the free amino group residues of the basic oligopeptide KKRKRKRKR.

Support for claim 28: The supramolecular nanoparticles according to claim 25, wherein the combinatorial carboxylated derivatives of basic oligopeptide KKRKRKRKR are derivatives which are carboxymethylated on between 1 to 9 of the free amino group residues of the basic oligopeptide KKRKRKRKR.

Support for claim 29: The supramolecular nanoparticles according to claim 25, wherein the combinatorial carboxylated derivatives of basic oligopeptide KKRKRKRKR are derivatives which are combinatorial mixtures which are succinylated, maleylated and carboxymethylated on between 1 to 9 of the free amino group residues of the basic oligopeptide KKRKRKRKR.

Support for claim 30: The supramolecular nanoparticles according to claim 2, wherein the binding component is poly-L-lysine.

Other aspects of the invention include methods of producing supramolecular structures by preparing a suspension of structural components and binding components and terminating components. Other aspects of the invention include selecting a ratio for amount of structural component(s) to binding component(s) to terminating component(s) for a purpose including selecting a size intended for the supramolecular structures. Advantageously, the structural component(s), the binding component(s) and the terminating component(s) may be capable of a self-assembly into preferred supramolecular structures with a substantially predetermined size.

Note that the meaning of the supramolecular relates to for example, supramolecular assembly and supramolecular structure meanings. A supramolecular assembly for example can be defined as a complex of molecules held together by noncovalent bonds. For example, a supramolecular assembly can be simply composed of two molecules (e.g., a DNA double helix or an inclusion compound) or a larger complex(es) of molecules forming for example, a sphere-, a rod-, or a sheet-like species, a nanoparticle or a discrete particle. Micelles, liposomes and biological membranes are also examples of some kinds of supramolecular assemblies. The dimensions of supramolecular assemblies conceivably has a wide possible range, for example for the present invention embodiments, a range between about 5 nanometers to about 10 microns. The present specification discloses size ranges for supramolecular assembles and structures individually or combinations of supramolecular structures (assembles) forming a nanoparticle. The general field of supramolecular chemistry is a domain of chemistry concerning chemical systems composed of a discrete number of molecules. The strength of the forces responsible for spatial organization of the system range from weak intermolecular forces, electrostatic charge, or hydrogen bonding to strong covalent bonding, provided that the electronic coupling strength remains small relative to the energy parameters of the component. Whereas traditional chemistry concentrates on the covalent bond, supramolecular chemistry additionally concerns weaker and reversible non-covalent interactions between molecules which consequently produce combinations of small molecules to for supermolecules or supramolecular assemblies wherein the number of supramolecular structures is conceived by Inventor and disclosed in the specification to be possibly a calculated or estimated number by using combinatorial chemistry and combinatorial mathematics calculations which have been disclosed in the present specification. Supramolecular assemblies form and may have an average life time sustained by/dependent upon hydrogen bonding, metal coordination, hydrophobic forces, van der Waals forces, pi-pi interactions and electrostatic effects between the small molecules which comprise the combinatorial supramolecular assemblies. Supramolecular chemistry also concerns dynamic (spontaneous, energy-dependent, entropic and thermodynamic processes) molecular self-assembly, molecular folding, molecular recognition, host-guest chemistry, mechanically-interlocked molecular architectures, and dynamic covalent chemistry. The fundamentals of these ideas about supramolecular science are founded in prior art teachings as has been disclosed in the Background of the Specification. The meaning of supramolecular soluble systems, includes supramolecular soluble systems as a whole and includes solubility of their components, and solubility of the assembly and its components at various stages in the assembly process forming the supramolecular assemblies (structures).

Note that the meaning of a nanoparticle includes meanings for an ultrafine particle and/or a discrete particle. A nanoparticle in some invention embodiments of the present invention has a largest dimension which between 1 nanometer and 10,000 nanometers. The structural, binding and terminating components self-assemble into supramolecular structures having a substantially predetermined size. Preferably, in some cases, the predetermined size is preferably at least about 10 nm and less than about 800 nm (nanometers). In some embodiments of the present invention, the predetermined size is between about 5 nm to 2000 nm. Preferably in some embodiments of the present invention, the predetermined size is at least about 20 nm and less than about 400 nm (nanometers). A nanoparticle's median absolute/or hydrated largest dimension can be measured in a liquid by direct laser scanning (DLS) using a Malvern Instruments Zetasizer to calculate the dimensions. Optical and or X-ray technology, or testing using a nanometer and/or micron filter filtration membrane methods known in the prior art can also be helpful for characterizing a median size or a relative size of nanoparticles.

Where a term is provided in the singular, the inventors also contemplate aspects of the invention described by the plural of that term. Thus, for example, a reference to "a method" includes one or more methods, and/or steps of the type described herein and/or which will become apparent to those persons skilled in the art upon reading this disclosure. Unless defined otherwise, all technical and scientific terms used herein include at least the same meaning as commonly understood by one of ordinary skill in the art to which this invention belongs. All publications mentioned herein are incorporated herein by reference in their entirety. Where there are discrepancies in terms and definitions used in references that are incorporated by reference or in future publications, the terms used in this patent application shall have the meaning as given herein. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. Supramolecular nanoparticles, comprising: a combination of nanostructures selected from the group consisting of combinatorial carboxylated cobalamins obtained from a first combinatorial synthesis, combinatorial carboxylated dipyridamoles obtained from a second combinatorial synthesis, basic amino acid polypeptides obtained from a third combinatorial synthesis, and any combination thereof.

2. The supramolecular nanoparticles according to claim 1, wherein the supramolecular nanoparticles have antiviral properties, wherein the supramolecular nanoparticles further comprise dynamic self-organizing soluble nanostructures, and wherein the nanostructures further comprise a plurality of binding components, a plurality of organic cores, and a plurality of terminating components.

3. The supramolecular nanoparticles according to claim 2, wherein one of the binding components further comprises combinatorial carboxylated cobalamins which have a number of binding regions, wherein the organic cores further comprise the combinatorial carboxylated dipyridamoles which have at least one binding element adapted for binding to the combinatorial carboxylated cobalamins, wherein the organic cores further comprise mechanical structures for the dynamic self-organizing soluble nanostructures, and wherein the binding of the combinatorial carboxylated cobalamins to the combinatorial carboxylated dipyridamoles can further comprise first inclusion complexes.

4. The supramolecular nanoparticles according to claim 3, wherein the terminating components each have at least one terminating binding element that binds to a remaining binding region of one of the binding components and can further comprise second inclusion complexes.

5. The supramolecular nanoparticles according to claim 4, wherein the basic amino acid polypeptides further comprise carboxylated basic amino acids of basic amino acids selected from the group consisting of lysine, histidine, arginine, derivatized lysine, derivatized histidine, derivatized arginine, acylated lysine, acylated histidine, acylated arginine, and any combination of basic amino acids thereof.

6. The supramolecular nanoparticles according to claim 5, wherein the plurality of terminating components occupy the remaining binding regions of the plurality of binding components, wherein the plurality of terminating components are in a quantity relative to the plurality of the binding regions of the plurality of the binding components so as to terminate further binding of binding components, and wherein the supramolecular nanoparticles further comprise discrete nanoparticles based on the dynamic self-organizing soluble nanostructures.

7. The supramolecular nanoparticles according to claim 1, wherein the combinatorial carboxylated cobalamins are a succinylated cyanocobalamins mixture.

8. The supramolecular nanoparticles according to claim 1, wherein combinatorial carboxylated cobalamins are a succinylated methyl cobalamins mixture.

9. The supramolecular nanoparticles according to claim 1, wherein combinatorial carboxylated cobalamins are a succinylated hydroxycobalamins mixture.

10. The supramolecular nanoparticles according to claim 1, wherein combinatorial carboxylated cobalamins are a succinylated cobamides mixture.

11. The supramolecular nanoparticles according to claim 1, wherein combinatorial carboxylated cobalamins are selected from the group consisting of succinylated hydroxycobalam ins mixtures, succinylated cobamides mixtures, succinylated hydroxycobalamins mixtures, succinylated methyl cobalamins mixtures, succinylated cyanocobalamins mixtures, and any combination thereof.

12. The supramolecular nanoparticles according to claim 2, wherein at least one of the organic cores further comprises at least one element selected from a photo-dynamic component which is supramolecular combinatorial carboxylated riboflavins.

13. The supramolecular nanoparticles according to claim 12, wherein the supramolecular combinatorial carboxylated riboflavins are supramolecular combinatorial succinylated riboflavins.

14. The supramolecular nanoparticles according to claim 12, wherein the supramolecular combinatorial carboxylated riboflavins are supramolecular combinatorial succinylated flavin mononucleotides.

15. The supramolecular nanoparticles according to claim 12, wherein the supramolecular combinatorial carboxylated riboflavins are supramolecular combinatorial succinylated flavin dinucleotides.

16. The supramolecular nanoparticles according to claim 1, wherein the combinatorial carboxylated dipyridamoles are supramolecular succinylated combinatorial dipyridamoles.

17. The supramolecular nanoparticles according to claim 1, wherein the combinatorial carboxylated dipyridamoles are supramolecular maleylated combinatorial dipyridamoles.

18. The supramolecular nanoparticles according to claim 1, wherein the combinatorial carboxylated dipyridamoles are supramolecular carboxymethylated combinatorial dipyridamoles.

19. The supramolecular nanoparticles according to claim 5, wherein the carboxylated basic amino acids are selected from the group consisting of succinylated lysine, succinylated histidine, succinylated arginine, and any combination thereof.

20. The supramolecular nanoparticles according to claim 5, wherein carboxylated basic amino acids are selected from the group consisting of maleylated lysine, maleylated histidine, maleylated arginine, and any combination thereof.

21. The supramolecular nanoparticles according to claim 5, wherein carboxylated basic amino acids are selected from the group consisting of carboxymethylated lysine, carboxymethylated histidine, carboxymethylated arginine, and any combination thereof.

22. The supramolecular nanoparticles according to claim 5, wherein carboxylated basic amino acids are selected from the group consisting of carboxymethylated lysine, carboxymethylated histidine, carboxymethylated arginine, succinylated lysine, succinylated histidine, succinylated arginine, maleylated lysine, maleylated histidine, maleylated arginine, and any combination thereof.

23. The supramolecular nanoparticles according to claim 4, wherein the plurality of the terminating components comprise at least one terminating component selected from the group consisting of a polyethylene glycol, a polymer, a polypeptide, a oligosaccharide, and any combination thereof.

24. The supramolecular nanoparticles according to claim 3, wherein the organic cores comprise at least one organic core selected from the group consisting of a dendrimer, a branched polyethyleneimine, a linear polyethyleneimine, a polylysine, a polylactide, apolylactide-co-glycoside, a polyanhydride, a poly-ε-caprolactone, a polymethyl methacrylate, a poly (N-isopropyl acrylamide), and a polypeptide, and any combination thereof.

25. The supramolecular nanoparticles according to claim 2, wherein at least one of the plurality of the binding components further comprises combinatorial carboxylated derivatives of the basic oligopeptide KKRKRKRKR.

26. The supramolecular nanoparticles according to claim 25, wherein the combinatorial carboxylated derivatives of the basic oligopeptide KKRKRKRKR are derivatives which are succinylated on between 1 to 9 of the free amino group residues of the basic oligopeptide KKRKRKRKR.

27. The supramolecular nanoparticles according to claim 25, wherein the combinatorial carboxylated derivatives of basic oligopeptide KKRKRKRKR are derivatives which are maleylated on between 1 to 9 of the free amino group residues of the basic oligopeptide KKRKRKRKR.

28. The supramolecular nanoparticles according to claim 25, wherein the combinatorial carboxylated derivatives of basic oligopeptide KKRKRKRKR are derivatives which are carboxymethylated on between 1 to 9 of the free amino group residues of the basic oligopeptide KKRKRKRKR.

29. The supramolecular nanoparticles according to claim 25, wherein the combinatorial carboxylated derivatives of basic oligopeptide KKRKRKRKR are derivatives which are combinatorial mixtures which are succinylated, maleylated and carboxymethylated on between 1 to 9 of the free amino group residues of the basic oligopeptide KKRKRKRKR.

30. The supramolecular nanoparticles according to claim 2, wherein the binding component is poly-L-lysine.

* * * * *